(12) United States Patent
Jung et al.

(10) Patent No.: US 8,404,435 B2
(45) Date of Patent: Mar. 26, 2013

(54) ENIGMA-MDM2 INTERACTION AND USES THEREOF

(75) Inventors: Cho-Rok Jung, Daejeon (KR); Dong-Soo Im, Daejeon (KR); Jung-Hwa Lim, Cheongju (KR); Yoon Jung Choi, Daejeon (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 0 days.

(21) Appl. No.: 13/240,351

(22) Filed: Sep. 22, 2011

(65) Prior Publication Data

US 2012/0015374 A1    Jan. 19, 2012

Related U.S. Application Data

(62) Division of application No. 12/704,226, filed on Feb. 11, 2010, now Pat. No. 8,088,750.

(30) Foreign Application Priority Data

Mar. 19, 2009 (KR) ........................ 10-2009-0023510

(51) Int. Cl.
*C12Q 1/68* (2006.01)
*G01N 33/53* (2006.01)

(52) U.S. Cl. ............................ 435/4; 435/7.1; 435/7.23

(58) Field of Classification Search ........................ None
See application file for complete search history.

(56) References Cited

U.S. PATENT DOCUMENTS

| | | | |
|---|---|---|---|
| 2004/0009946 | A1 | 1/2004 | Lewis et al. |
| 2006/0088532 | A1 | 4/2006 | Alitalo et al. |
| 2008/0305493 | A1 | 12/2008 | Strovel et al. |

OTHER PUBLICATIONS

Jung et al, J Clin Inves 120: 4493-4506, 2010.*
Wu et al, Lab Inves 84:1547-1556, 2004.*
Bach, "The LIM domain: regulation by association," *Mechanisms of Development*, vol. 91, pp. 5-17, 2000.
Durick et al., "Shc and Enigma Are Both Required for Mitogenic Signaling by Ret/ptc2," *Molecular and Cellular Biology*, vol. 18, No. 4, pp. 2298-2308, 1998.
Fang et al., "Mdm2 Is a RING Finger-dependent Ubiquitin Protein Ligase for Itself and p53," *Journal of Biological Chemistry*, vol. 275, No. 12, pp. 8945-8951, 2000.
Feng et al., "Stabilization of Mdm2 via Decreased Ubiquitination Is Mediated by Protein Kinase B/Akt-dependent Phosphorylation," *Journal of Biological Chemistry*, vol. 279, No. 34, pp. 35510-35517, 2004.
Haupt et al., "Mdm2 promotes the rapid degradation of p53," *Nature*, vol. 387, pp. 296-299, 1997.
Higashitsuji et al., "The oncoprotein gankyrin binds to MDM2/HDM2, enhancing ubiquitylation and degradation of p53," *Cancer Cell*, vol. 8, pp. 75-87, 2005.
Honda et al., "Oncoprotein MDM2 is a ubiquitin ligase E3 for tumor suppressor p53," *FEBS Letters*, vol. 420, pp. 25-27, 1997.
Honda and Yasuda, "Activity of MDM2, a ubiquitin ligase, toward p53 or itself is dependent on the RING finger domain of the ligase," *Oncology*, vol. 19, pp. 1473-1476, 2000.
Kuroda et al., "Protein-Protein Interaction of Zinc Finger LIM domains with Protein Kinase C," *Journal of Biological Chemistry*, vol. 271, No. 49, pp. 31029-31032, 1996.
Michael and Oren, "The p53-Mdm2 module and the ubiquitin system," *Seminars in Cancer Biology*, vol. 13, pp. 49-58, 2003.
Onel and Cordon-Cardo, "MDM2 and Prognosis," *Molecular Cancer Research*, vol. 2, pp. 1-8, 2004.
Sui et al., "Yin Yang 1 Is a Negative Regulator of p53," *Cell*, vol. 117, pp. 859-872, 2004.
Tang et al., "Critical role for Daxx in regulating Mdm2," *Nature Cell Biology*, vol. 8, No. 8, pp. 855-862, 2006 and Supplementary Information pp. 1-5.
Tilesi et al., "Design and validation of siRNAs and shRNAs," *Current Opinion in Molecular Therapeutics*, vol. 11, No. 2, pp. 156-164, 2009.
Wu et al., "Specificity of LIM Domain Interactions with Receptor Tyrosine Kinases," *Journal of Biological Chemistry*, vol. 271, No. 27, pp. 159341-15941, 1996.

* cited by examiner

*Primary Examiner* — Lei Yao

(74) *Attorney, Agent, or Firm* — Klarquist Sparkman, LLP

(57) ABSTRACT

The present invention relates to Enigma (PDLIM7)-Mdm2 interaction and use thereof. More particularly, it may induce an effective apoptosis of cancer cells by inhibition of an Enigma expression or an Enigma activity which induces Mdm2 destabilization and p53 activity; it may assess the prognosis of anti-cancer therapy by determining that Enigma, which is induced by SRF, is overexpressed in cancer tissues with Mdm2; it may screen anti-cancer activity substances by selecting a factor to inhibit specific binding between Enigma and Mdm2. Enigma-Mdm2 interaction and Enigma expression regulation may be utilized usefully for preventing cancers and developing therapeutic methods and anti-cancer agents.

4 Claims, 21 Drawing Sheets

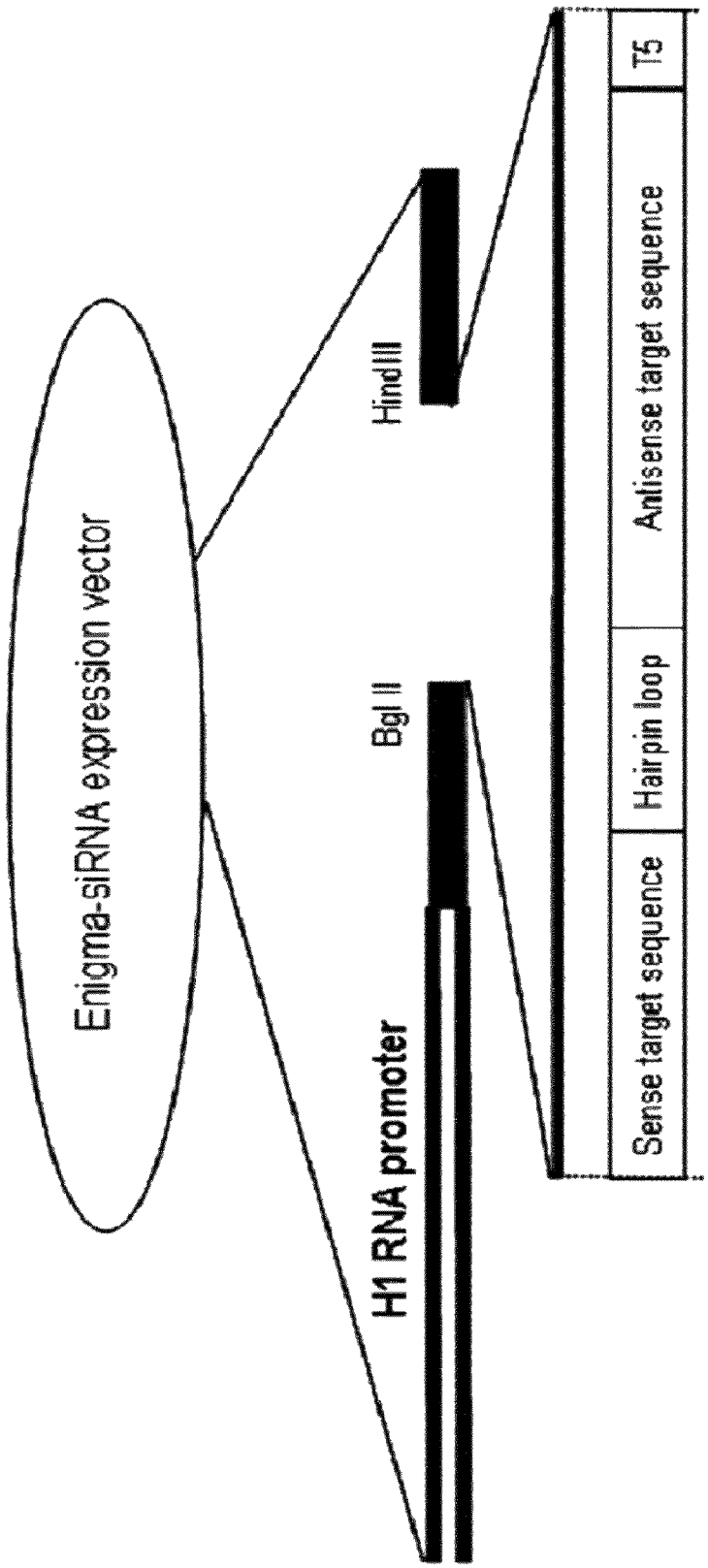

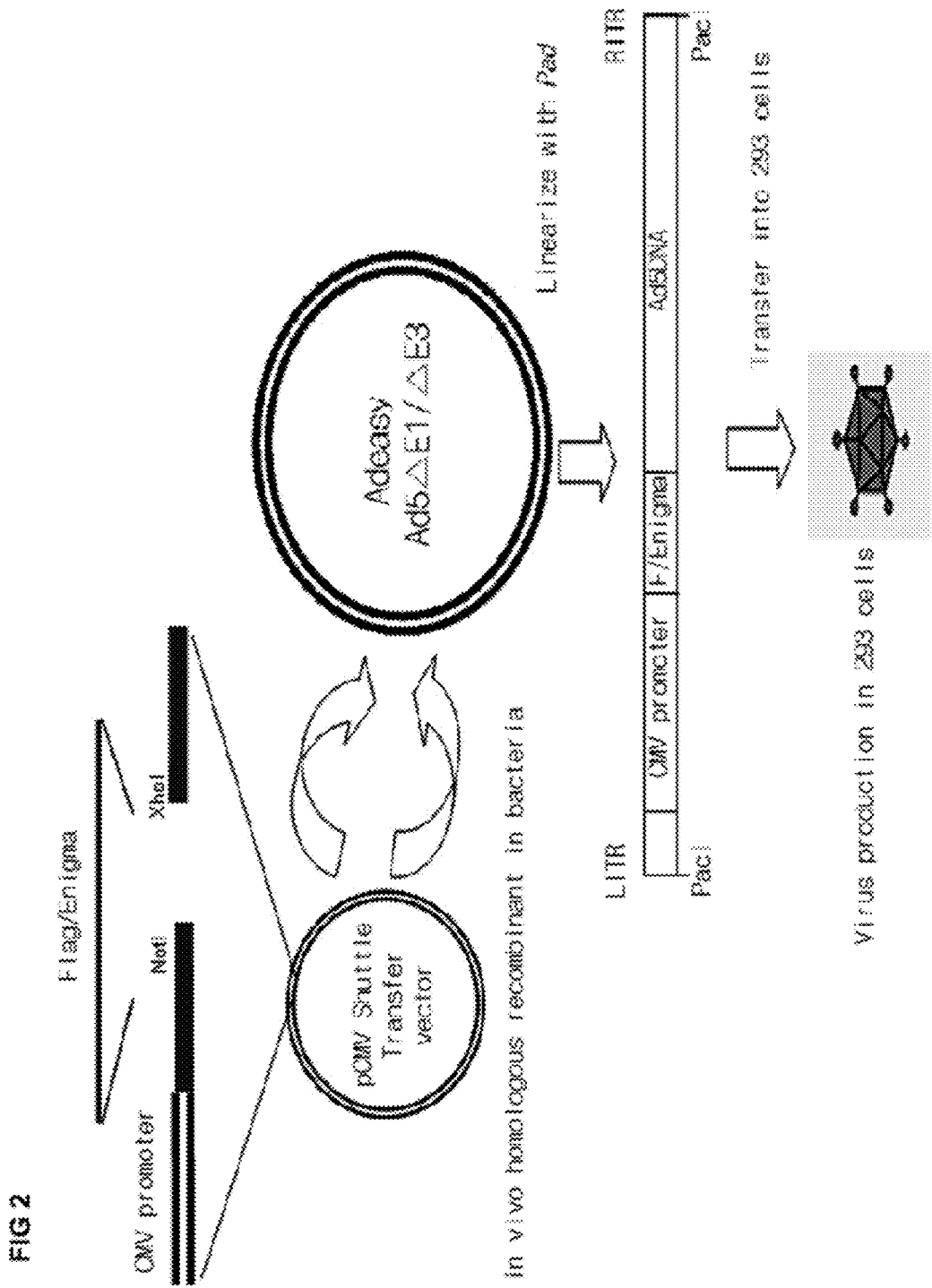

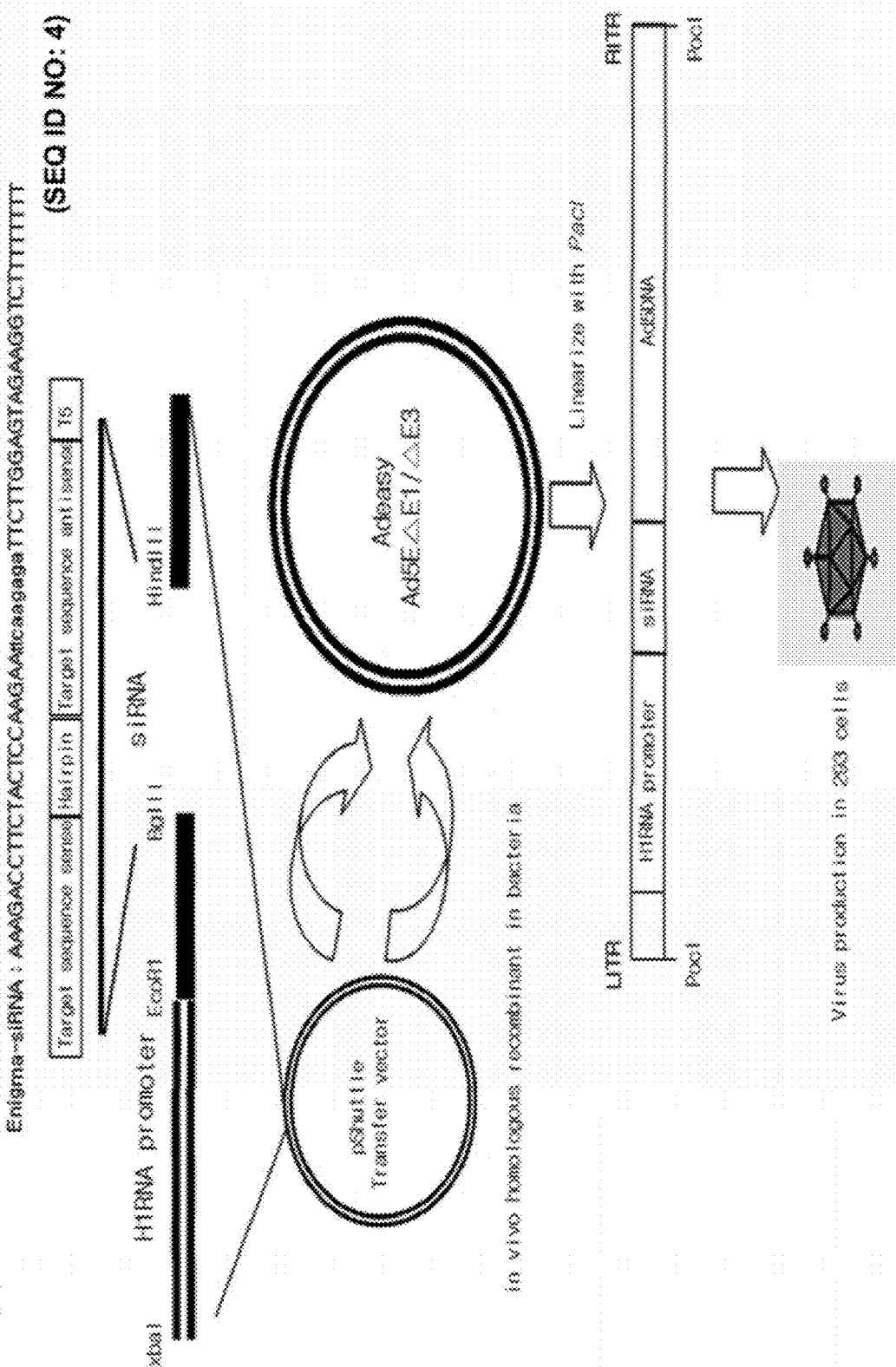

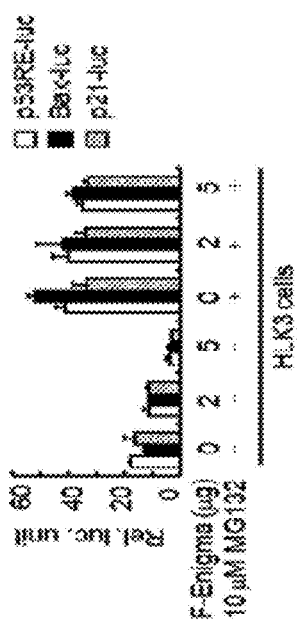
FIG 4A
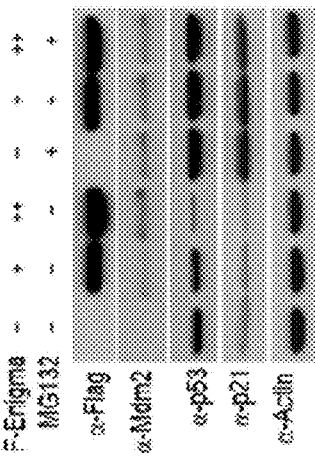
FIG 4B
FIG 4C
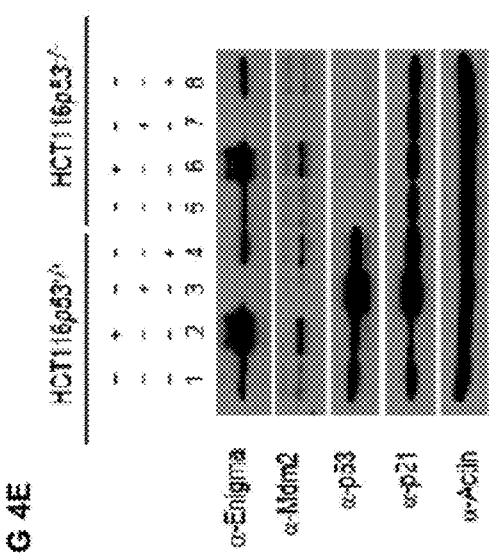
FIG 4E
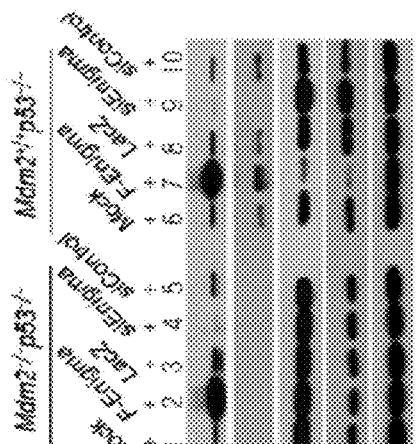
FIG 4D
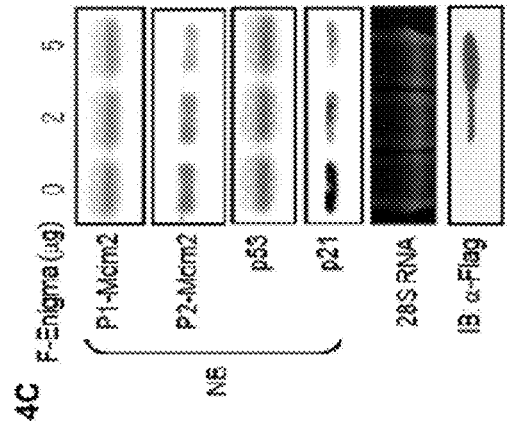

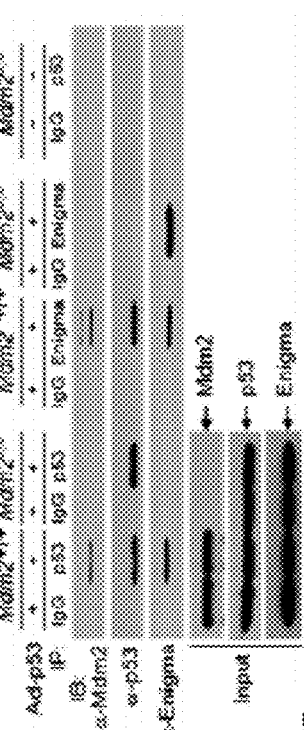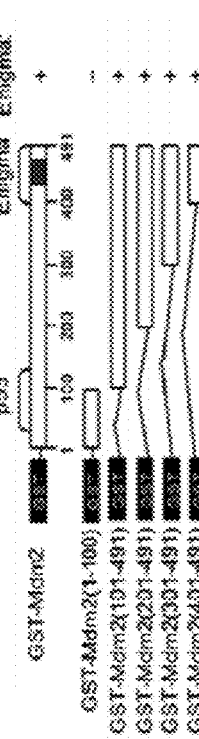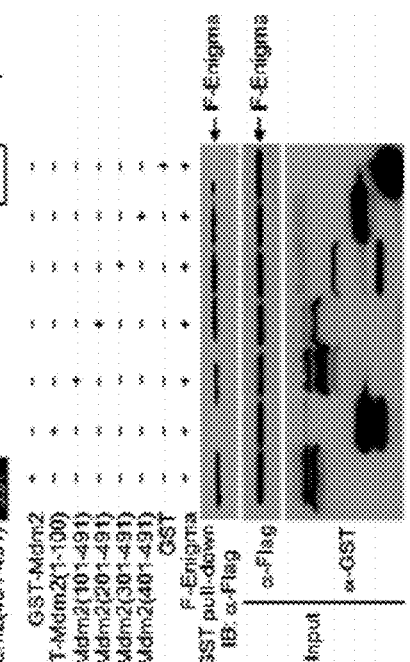
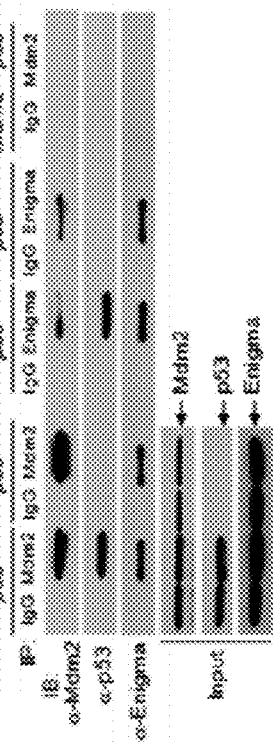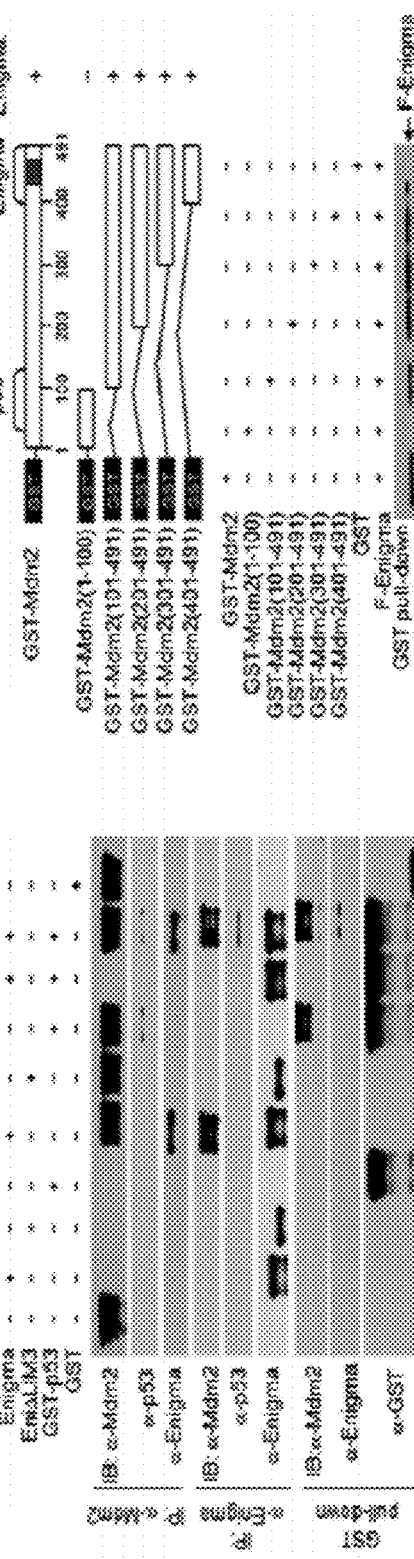
FIG 5A
FIG 5B
FIG 5C
FIG 5D

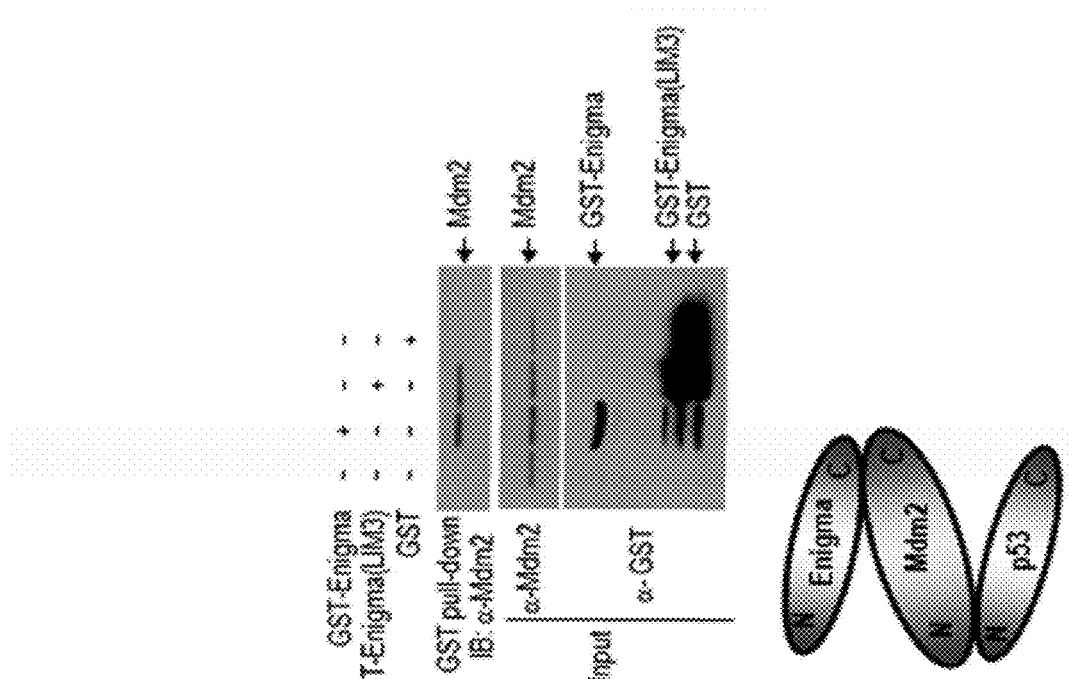

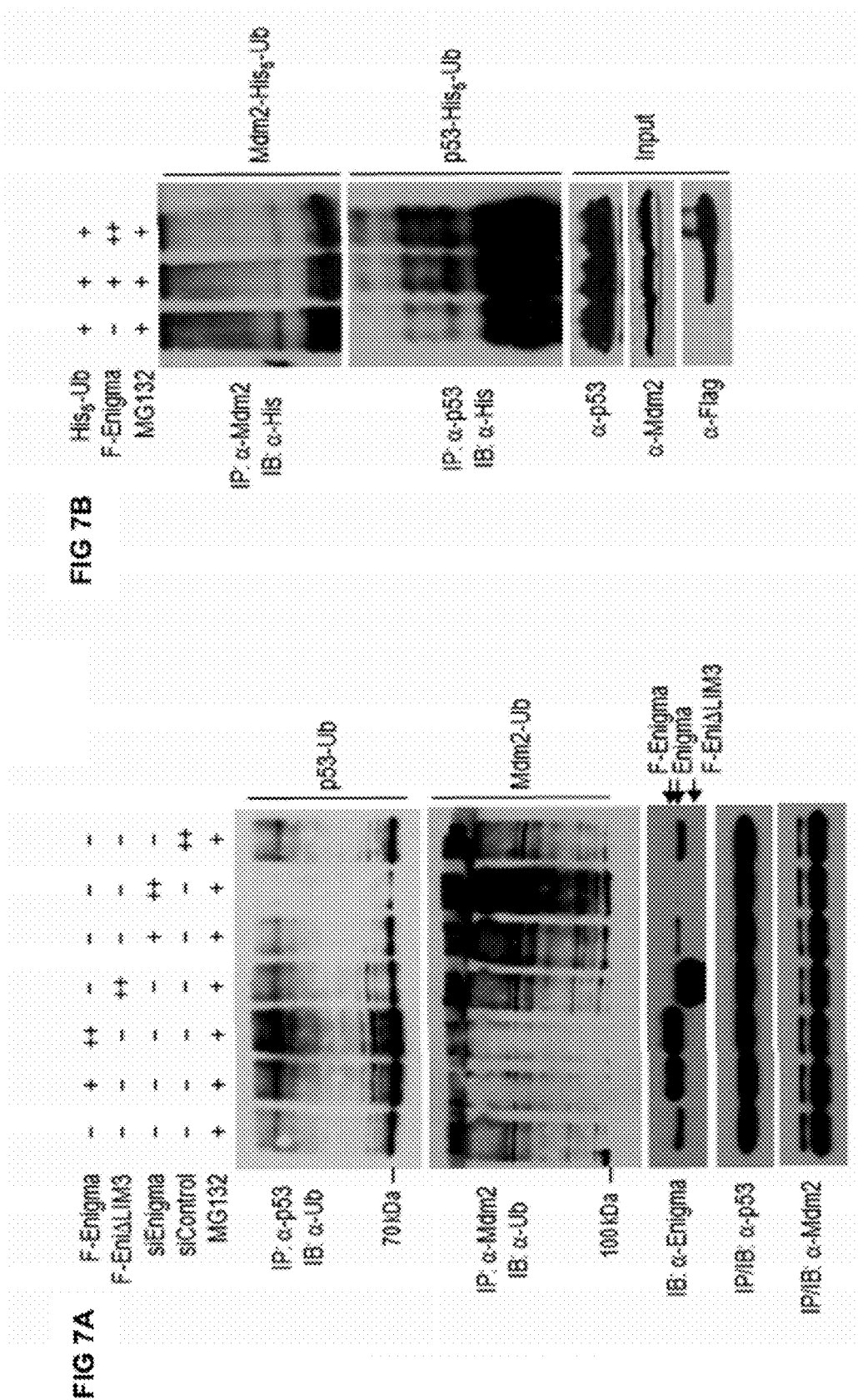

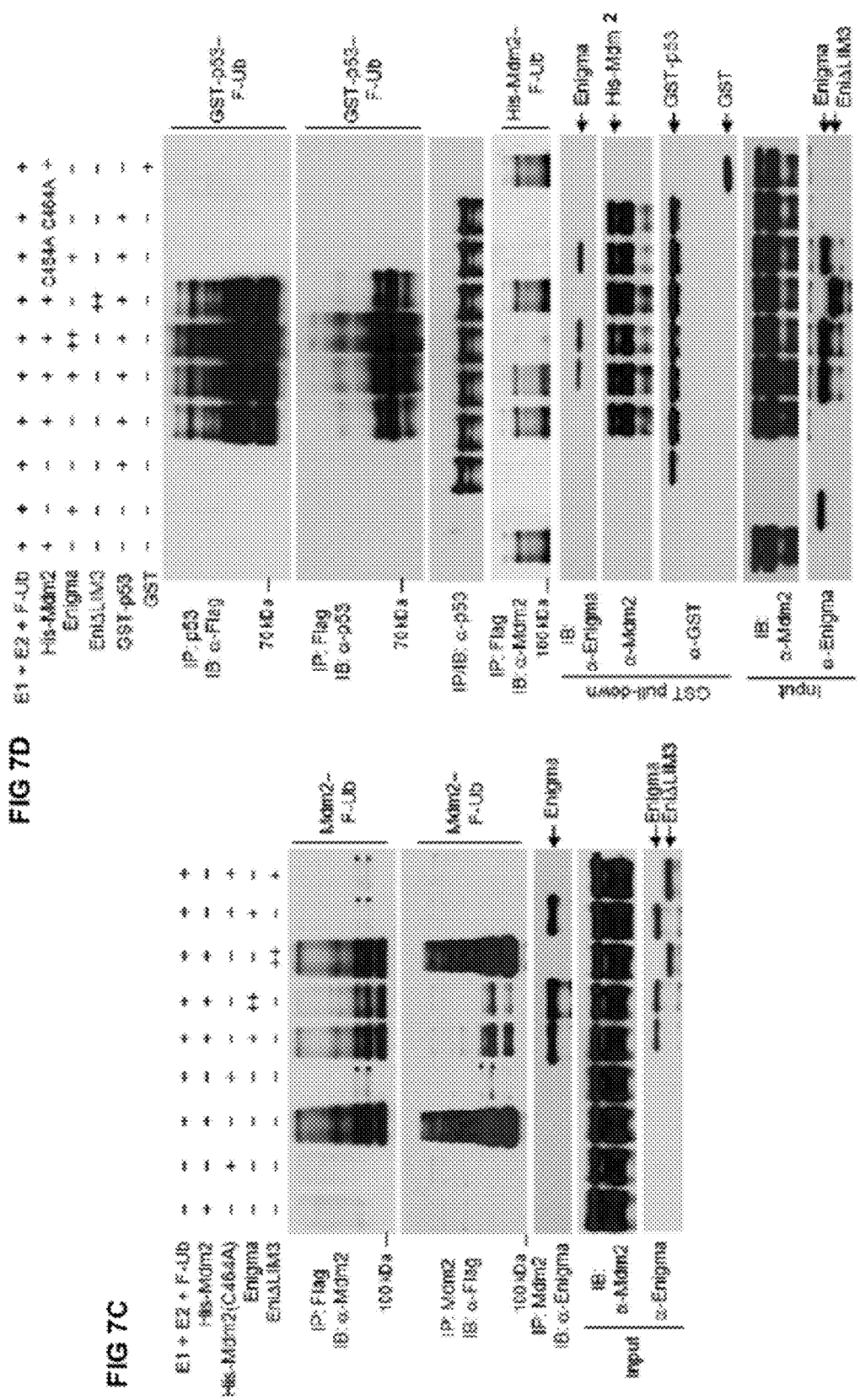

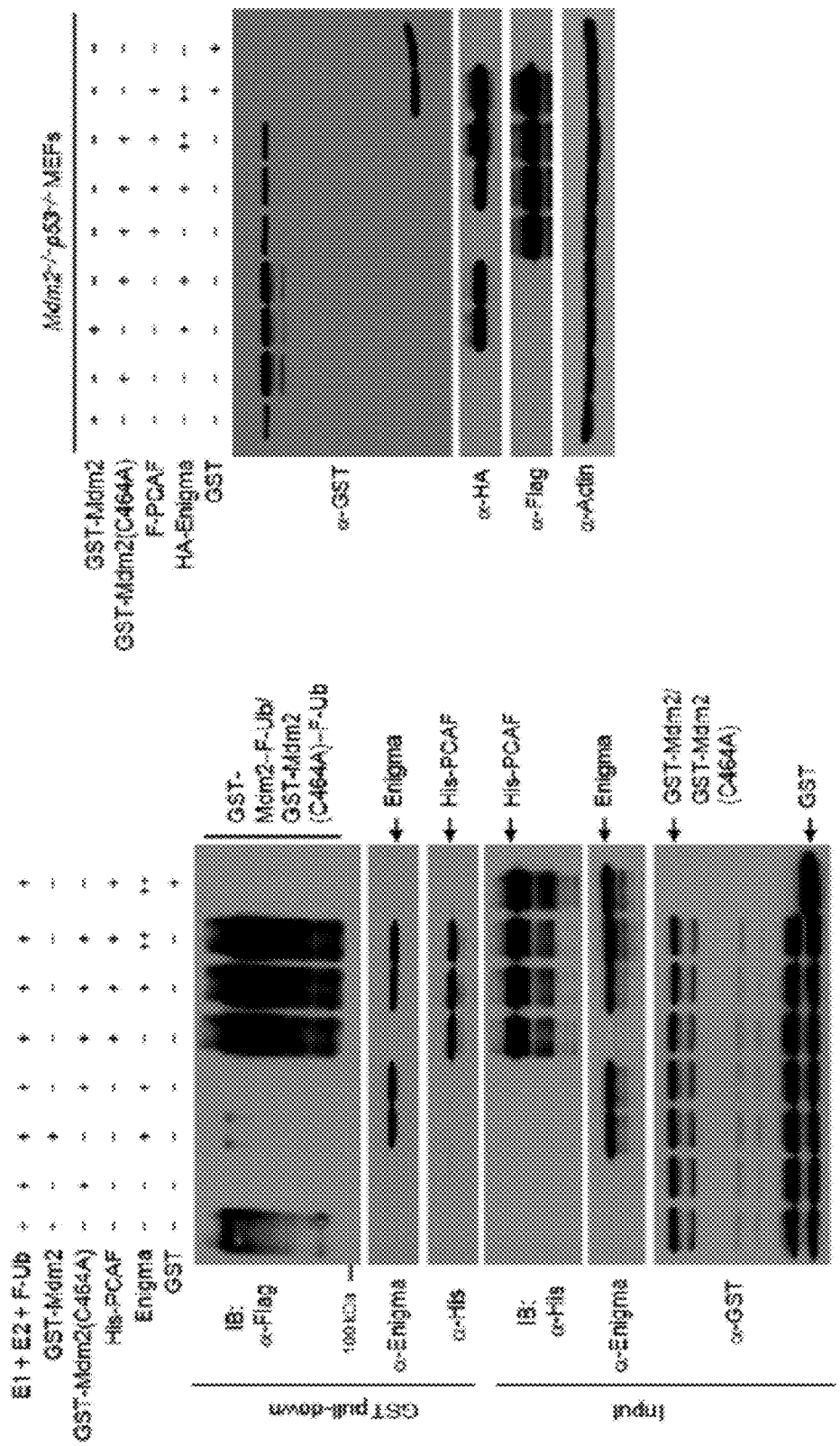

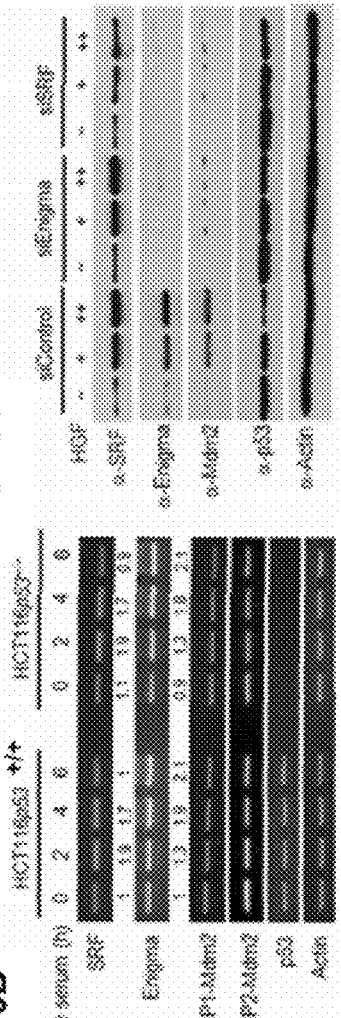
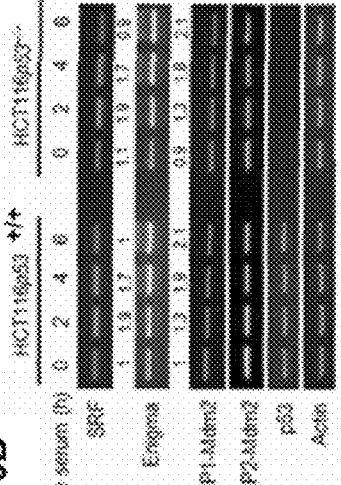
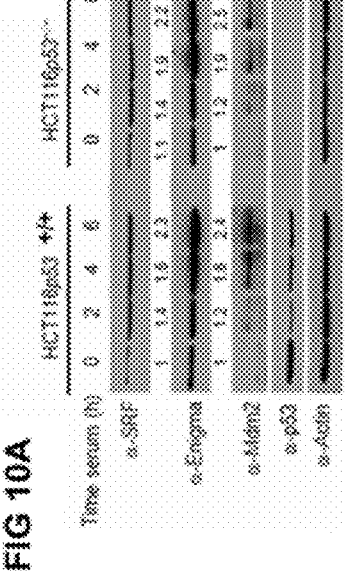
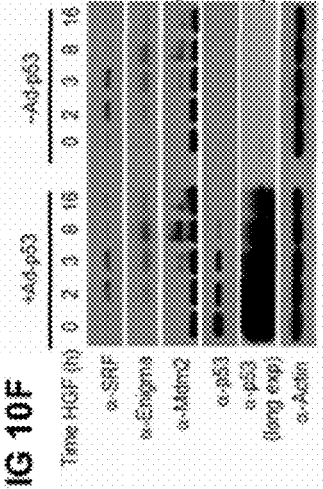
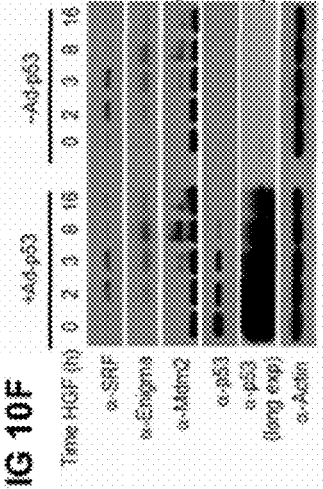
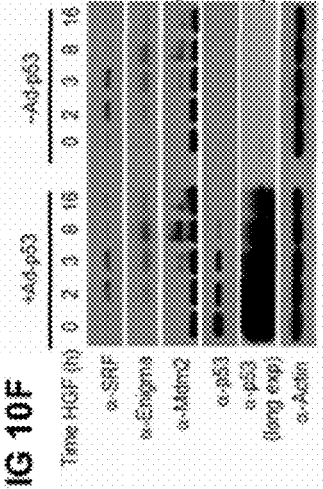
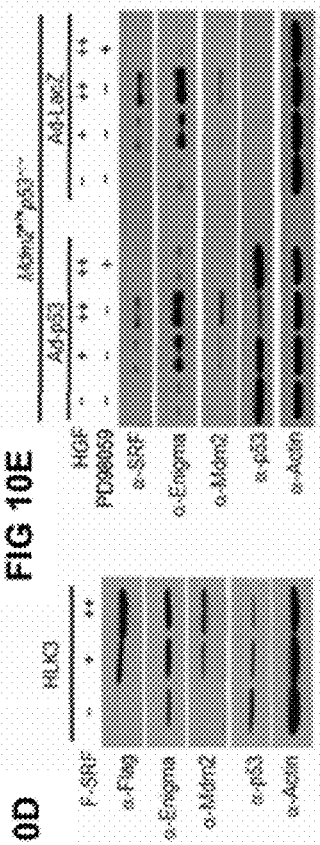
FIG 10A, FIG 10B, FIG 10C, FIG 10D, FIG 10E, FIG 10F, FIG 10G, FIG 10H

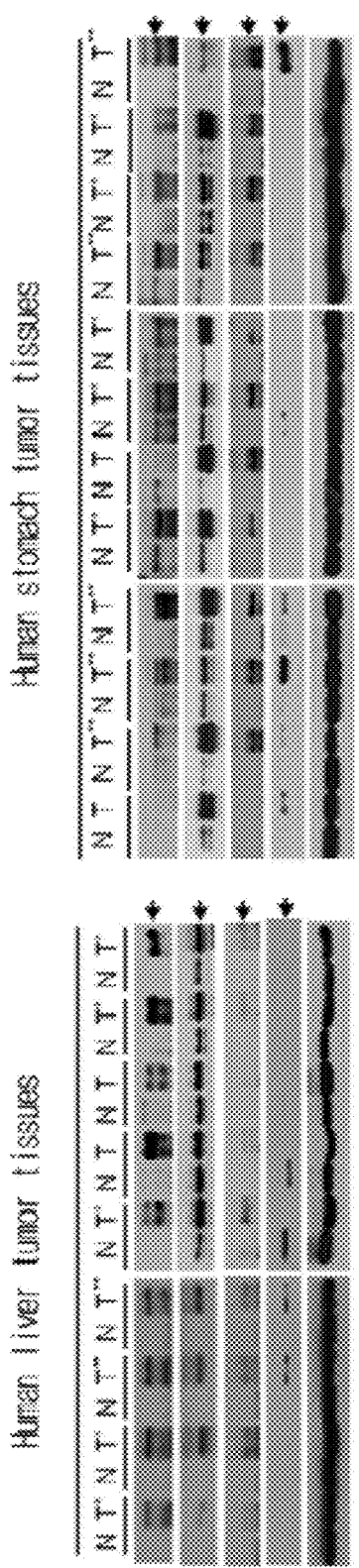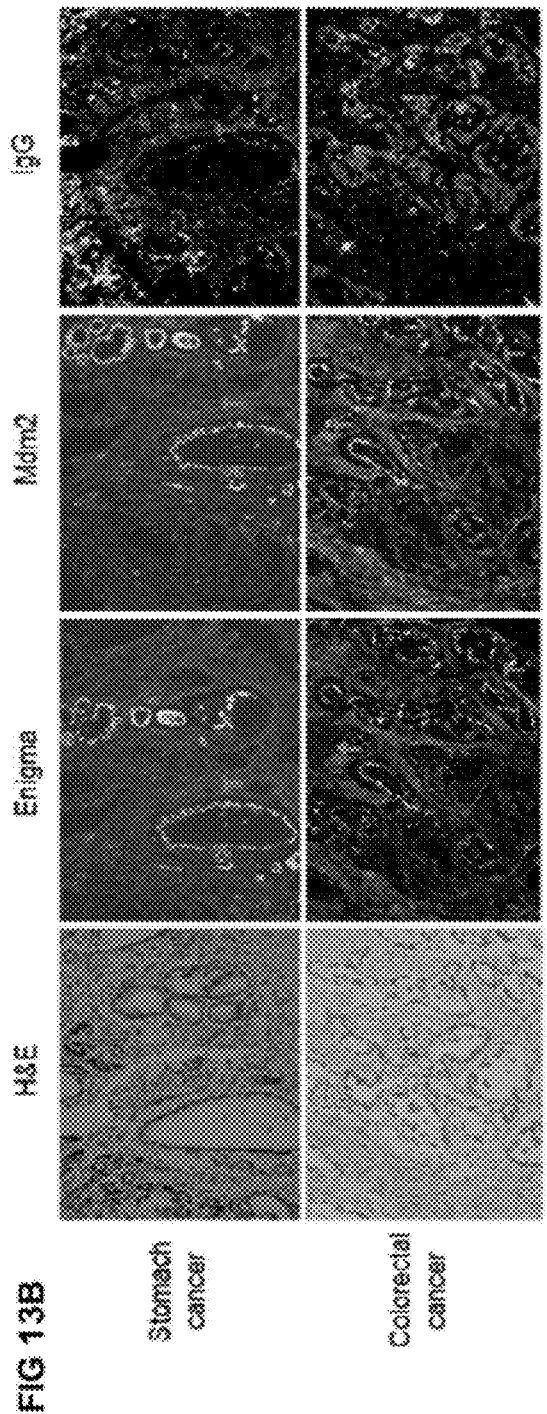
FIG 13A
FIG 13B

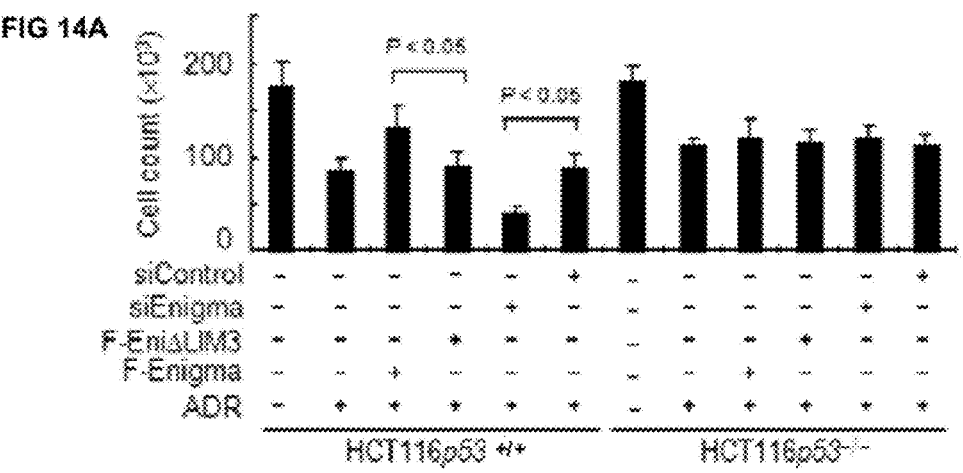
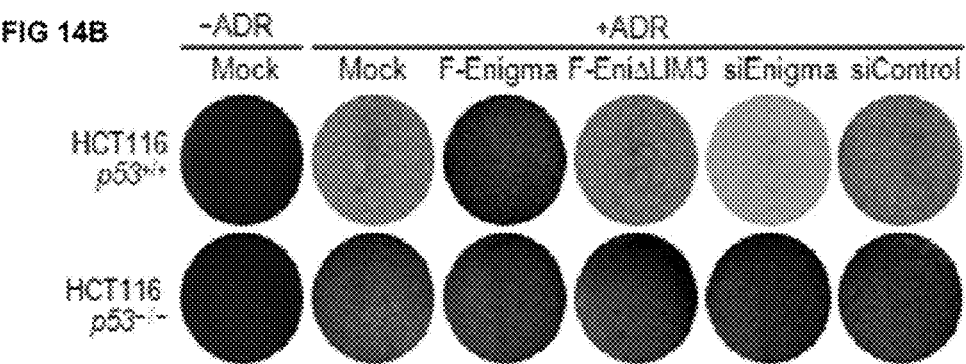
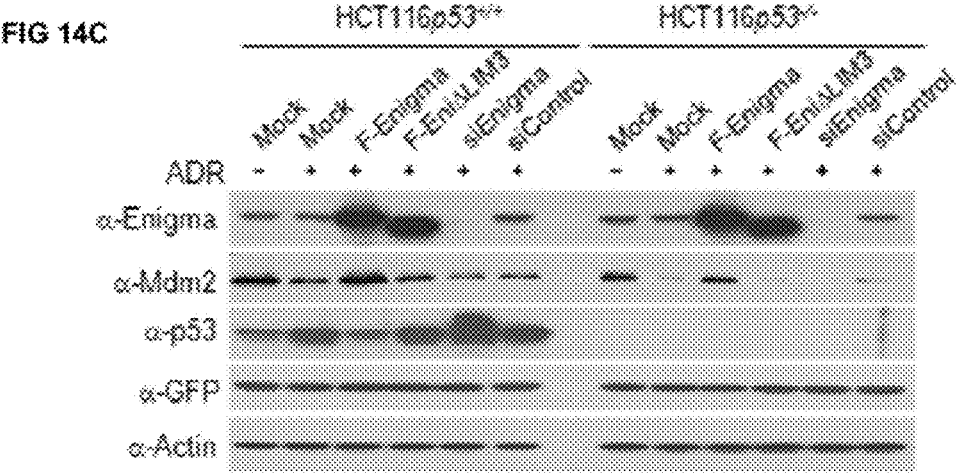

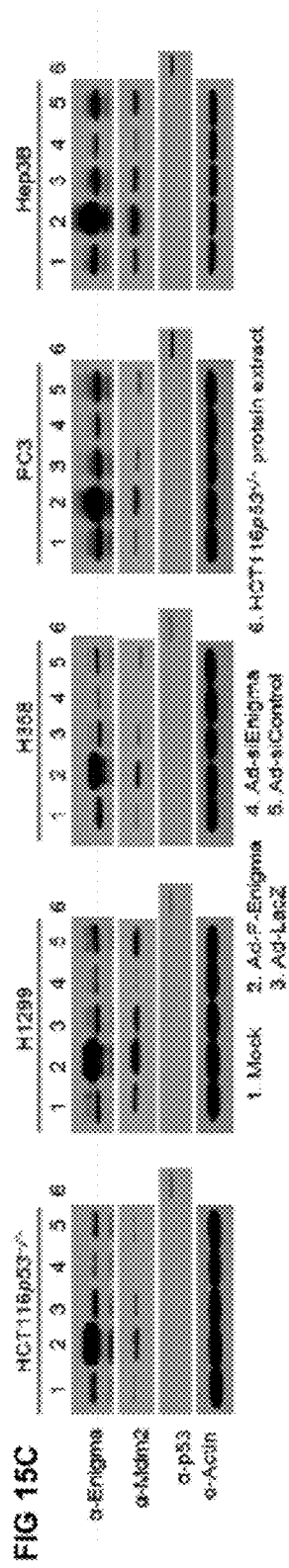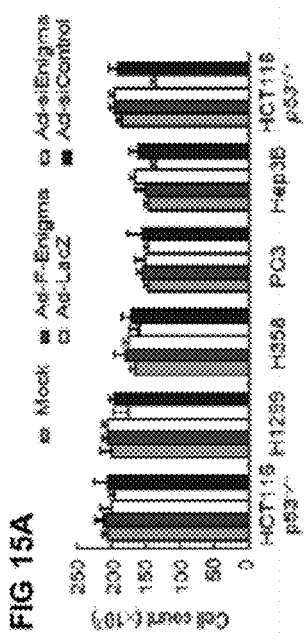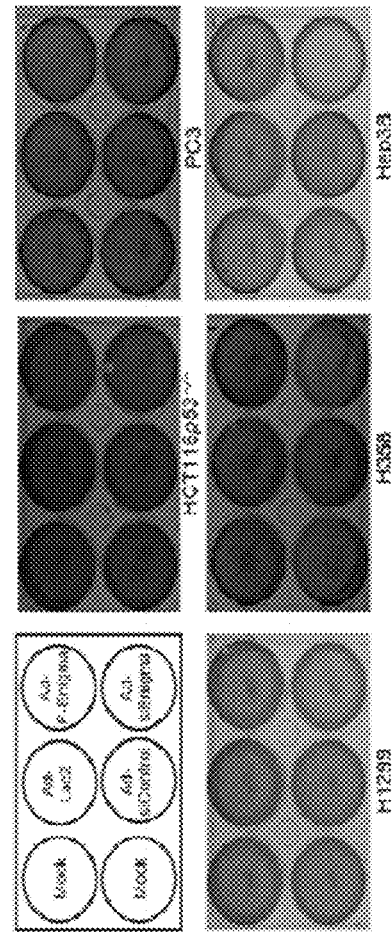
FIG 15A
FIG 15B
FIG 15C
FIG 15D

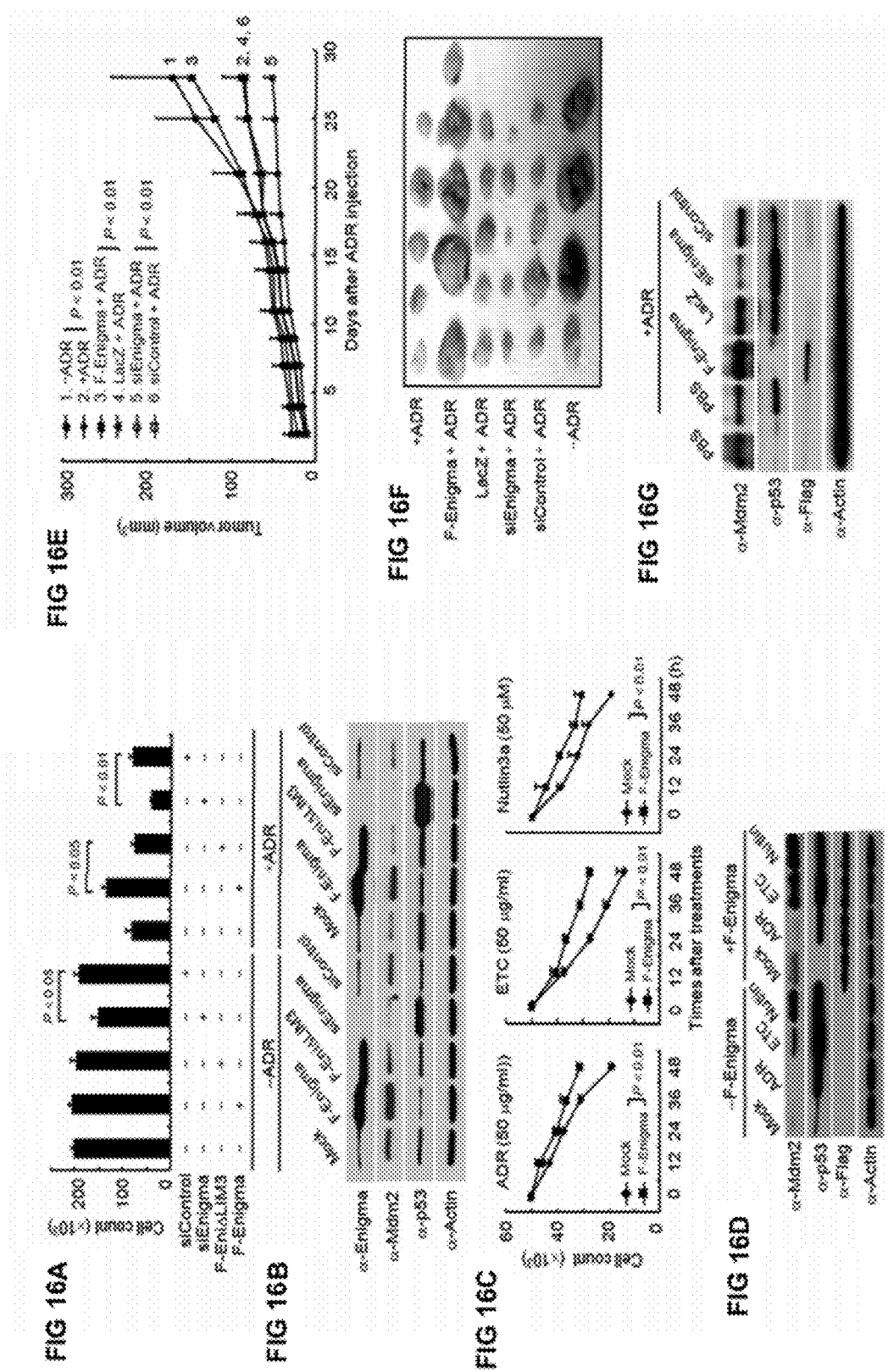

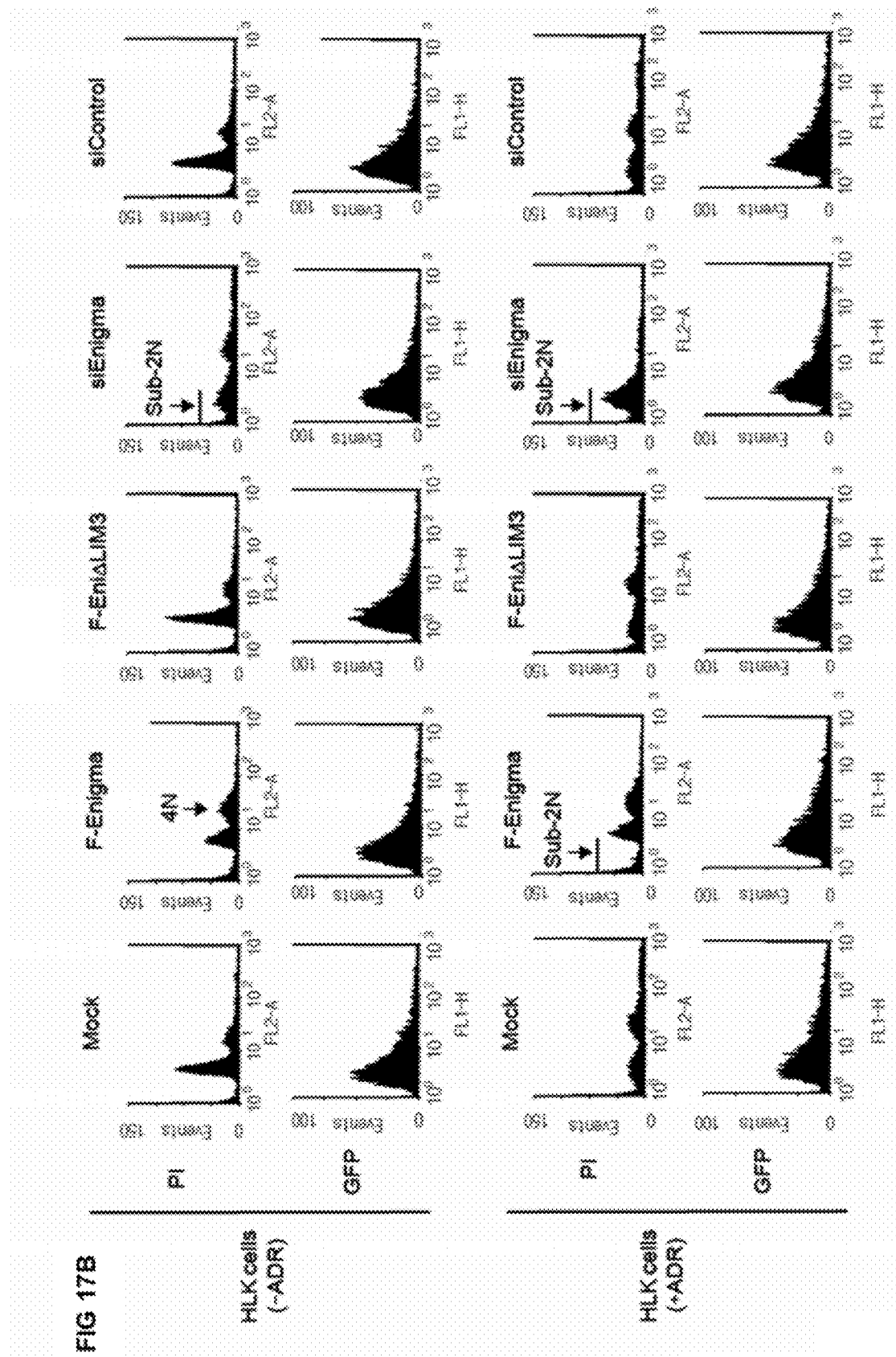

SEQUENCE LISTING

```
<160> NUMBER OF SEQ ID NOS: 5

<210> SEQ ID NO 1
<211> LENGTH: 1374
<212> TYPE: DNA
<213> ORGANISM: Homo sapiens

<400> SEQUENCE: 1
atggattcct tcaaagtagt gctggagggg ccagcacctt ggggcttccg gctgcaaggg      60
ggcaaggact tcaatgtgcc cctctccatt tcccggctca ctcctggggg caaagcggcg     120
caggccggag tggccgtggg tgactgggtg ctgagcatcg atggcgagaa tgcgggtagc     180
ctcacacaca tcgaagctca gaacaagatc cgggcctgcg gggagcgcct cagcctgggc     240
ctcagcaggg cccagccggt tcagagcaaa ccgcagaagg cctccgcccc cgccgcggac     300
cctccgcggt acacctttgc acccagcgtc tccctcaaca agacggcccg gccctttggg     360
gcgcccccgc ccgctgacag cgccccgcag cagaatggac agccgctccg accgctggtc     420
ccagatgcca gcaagcagcg gctgatggag aacacagagg actggcggcc gcggccgggg     480
acaggccagt cgcgttcctt ccgcatcctt gcccacctca caggcaccga gttcatgcaa     540
gacccggatg aggagcacct gaagaaatca agccaggtgc ccaggacaga agccccagcc     600
ccagcctcat ctacacccca ggagccctgg cctggcccta ccgcccccag ccctaccagc     660
cgcccgccct gggctgtgga ccctgcgttt gccgagcgct atgccccgga caaaacgagc     720
acagtgctga cccggcacag ccagccggcc acgcccacgc cgctgcagag ccgcacctcc     780
attgtgcagg cagctgccgg aggggtgcca ggaggggca gcaacaacgg caagactccc     840
gtgtgtcacc agtgccacaa ggtcatccgg ggccgctacc tggtggcgct gggccacgcg     900
taccacccgg aggagtttgt gtgtagccag tgtgggaagg tcctggaaga gggtggcttc     960
tttgaggaga agggcgccat cttctgccca ccatgctatg acgtgcgcta tgcacccagc    1020
tgtgccaagt gcaagaagaa gattacaggc gagatcatgc acgccctgaa gatgacctgg    1080
cacgtgcact gctttacctg tgctgcctgc aagacgccca tccggaacag ggccttctac    1140
```

-continued

```
atggaggagg gcgtgccctc ttgcgagcga gactatgaga agatgtttgg cacgaaatgc    1200
catggctgtg acttcaagat cgacgctggg gaccgcttcc tggaggccct gggcttcagc    1260
tggcatgaca cctgcttcgt ctgtgcgata tgtcagatca acctggaagg aaagaccttc    1320
tactccaaga aggacaggcc tctctgcaag agccatgcct tctctcatgt gtga          1374
```

```
<210> SEQ ID NO 2
<211> LENGTH: 21
<212> TYPE: DNA
<213> ORGANISM: Homo sapiens

<400> SEQUENCE: 2
aaagaccttc tactccaaga a                                               21

<210> SEQ ID NO 3
<211> LENGTH: 10
<212> TYPE: DNA
<213> ORGANISM: Homo sapiens

<400> SEQUENCE: 3
ctatataagg                                                            10

<210> SEQ ID NO 4
<211> LENGTH: 56
<212> TYPE: DNA
<213> ORGANISM: Artificial Sequence
<220> FEATURE:
<223> OTHER INFORMATION: Synthetic oligonucleotide Enigma-siRNA

<400> SEQUENCE: 4
aaagaccttc tactccaaga attcaagaga ttcttggagt agaaggtctt tttttt         56

<210> SEQ ID NO 5
<211> LENGTH: 21
<212> TYPE: DNA
<213> ORGANISM: Artificial Sequence
<220> FEATURE:
<223> OTHER INFORMATION: Synthetic oligonucleotide - Enigma oligo

<400> SEQUENCE: 5
aatgccatgg ctgtgacttc a                                               21
```

ENIGMA-MDM2 INTERACTION AND USES THEREOF

CROSS-REFERENCE TO RELATED APPLICATION

This is a divisional of U.S. patent application Ser. No. 12/704,226, filed Feb. 11, 2010, now U.S. Pat. No. 8,088,750, issued Jan. 3, 2012, which claims the benefit of priority from Korean Patent Application No. 10-2009-0023510, filed on Mar. 19, 2009, both of which are incorporated herein by reference.

BACKGROUND OF THE INVENTION

1. Field of the Invention

The present invention relates to Enigma (PDLIM7)-Mdm2 interaction and use thereof, more particularly, to a method of treating cancer using interaction between Enigma (PDLIM7) and Mdm2, and regulation of Enigma expression, and an anti-cancer agent.

2. Description of the Related Art

The tumor suppressor p53, which regulates the genes associated with cell growth arrest and apoptosis, has been known as an essential factor preventing normal cells from becoming cancerous cells by removing abnormal cells (Michael and Oren, Cncer Biol., 13, 49-58, 2003). This function of p53 is very strictly regulated for the survival of normal cells, and Hdm2/Mdm2 (human/mouse double minute 2; hereinafter referred to as "Mdm2") plays a main role in the regulation. The Mdm2, which is an E3 ubiquitin ligase that ubquiquinates p53 for degradation, regulates protein level of p53 in the cell (Haupt et al., Nature, 387, 296-299, 1997; Honda et al., FEBS Lett., 420,25-27,1997). Furthermore, Mdm2 forms an autoregulatory loop where the Mdm2 expression is regulated by the transcriptional control of p53 (Michael and Oren, Cancer Biol., 13, 49-58, 2003). Also, the Mdm2 ubiquitinates Mdm2 itself for degradation (Fang et al., J. Biol. Chem., 275, 8945-8951, 2000; Honda and Yasuda, Oncogene, 19, 4173-4176, 2000).

The Mdm2 deactivates p53 or acts p53-independently as an oncogene and is actually overexpressed throughout various human cancer tissues (Onel, K & Cordon-Cardo, C. Mol Cancer Res 2, 1-8, 2004). Since a negative regulation of the Mdm2 function in a cancer cell with a wild type p53 may induce apoptosis of the cancer cell, Mdm2 has been a useful target for the development of anti-cancer agent (Onel, K & Cordon-Cardo, C. Mol Cancer Res 2, 1-8, 2004). However, the apoptosis resulting from p53 stabilization through the regulation of the Mdm2 function may cause serious side effects in normal cells as well as in cancer cells, and therefore the elucidation of a pathway in cancer cells is urgently needed to regulate Mdm2 selectively.

PDLIM7 protein Enigma has PDZ and LIM domains (Bach, Mech.Dev. 91, 5-17, 2000). The LIM domain of the Enigma consists of three zinc fingers and binds with protein kinases or factors associated with insulin signaling, etc. (Kuroda et al., J. Biol. Chem., 271, 31029-31032,1996; Wu et al., J. Biol. Chem., 271, 15934-15941,1994). Furthermore, Enigma binds with Ret/ptc associated with thyroid cancer to activate it (Durick et al., Mol. Cell. Biol., 18, 2298-2308, 1998). However, Enigma's function in a cell has not been clearly understood.

The factors such as YY1, Gankyrin, Daxx, etc. are known to stabilize Mdm2 and therefore to weaken the activity of p53. The YY1 binds with both Mdm2 and p53 to thereby promote the degradation of p53, and Gankyrin enhances the enzyme activity of Mdm2 to thereby promote the degradation of p53 (Sui et al., Cell, 117,859-872,2004; Higashitsuji et al., Cancer cell, 8,75-87, 2005). While the Daxx binds with Mdm2 to stabilize Mdm2 and inhibit p53, it does not affect the self-ubiquitination activity of Mdm2 (Tang et al., Nat. Cell. Biol., 8,855-862, 2006). Mdm2 expression increases as cells proliferate (Feng et al., J. Biol. Chem., 279, 35510-35517, 2004), and however, how this occurs is not clear.

Hence, as a result of investigation on Enigma functions, the present inventors revealed a novel Mdm2-p53 regulatory mechanism which is clearly distinct from the typical regulatory factors for an Mdm2-p53 pathway in that Enigma specifically inhibits the self-ubiquitination of Mdm2 by Mdm2-dependently binding to p53, and promotes the degradation of p53 by enhancing Mdm2-dependent p53 ubiquitination. Additionally, first revealed was that the conditions of cellular proliferation, and the existence of SRF-Enigma-Mdm2 pathway in human liver cancer and stomach cancer tissues may weaken p53. Also revealed was that the Enigma overexpression in a cell increases the cell survival ability and induces its resistance to anti-cancer agents. Thus, the present invention comes to completion by revealing that p53 can be activated by inhibiting the overexpression of Enigma in cancer cells, that anti-cancer agents can be screened by selecting inhibiting factors of the Enigma-Mdm2 interaction, and that identifying the Enigma expression level in treatment with anti-cancer agents maybe used for the identification of the anti-cancer effect.

SUMMARY OF THE INVENTION

An object of the present invention is to elucidate relationships between cellular function of Enigma and cancer initiation and progression, to provide a method and formulation to induce apoptosis of cancer cells by inhibiting Enigma expression, and to provide a method of screening candidate anti-cancer substances, using the interaction between Enigma and Mdm2 or the expression regulation of Mdm2 and p53 by Enigma.

In order to achieve the objects, the present invention provides an anti-cancer composition including Enigma expression or activity inhibitor as an effective ingredient.

The present invention also provides an anti-cancer adjuvant including Enigma expression or activity inhibitor as an effective ingredient.

The present invention also provides a method of treating cancer, including administrating an inhibitor of Enigma expression or activity in a pharmaceutically effective amount to an individual suffering from cancer.

The present invention also provides a method of preventing cancer, including administrating an inhibitor of Enigma expression or activity in a pharmaceutically effective amount to an individual.

The present invention also provides a method of decreasing Mdm2 stability and increase p53 activity by inhibiting Enigma expression or activity.

The present invention also provides a method of screening candidate anti-cancer substances, using the Enigma-dependent expression level of Mdm2 or p53.

The present invention also provides a method of screening candidate anti-cancer substances, using an interaction level between Enigma and Mdm2.

The present invention also provides a method of diagnosing cancers, identifying therapeutic results, or assessing prognosis, using an Enigma expression level in cancer cells.

The present invention also provides a kit in use for diagnosing cancers, identifying therapeutic results, or assessing prognosis, including an inhibitor of Enigma expression or activity.

The present invention also provides a use for utilizing an inhibitor of Enigma expression or activity for preparation of an anti-cancer composition.

The present invention also provides a use for utilizing an inhibitor of Enigma expression or activity for preparation of an anti-cancer adjuvant.

The present invention also provides a use for utilizing an inhibitor of Enigma expression or activity for manufacturing a kit in use for diagnosing cancers, identifying therapeutic results, or assessing prognosis.

BRIEF DESCRIPTION OF THE DRAWINGS

The above and other objects, features and other advantages of the present invention will be more clearly understood from the following detailed description taken in conjunction with the accompanying drawings, in which:

FIG. 1 is a schematic diagram which is indicative of illustrating a vector including siEnigma;

FIG. 2 is a schematic diagram which is indicative of illustrating a method of preparing adenovirus expressing F-Enigma;

FIG. 3 is a schematic diagram which is indicative of illustrating a method of preparing adenovirus containing siEnigma;

FIG. 4A is a Western blot image illustrating through degradation pathway of ubiquitin proteasome Mdm2 is stabilized and p53 is degraded when Enigma is expressed;

FIG. 4B is a graph showing that a decrease in a p53 protein by Enigma results in a decrease in p53 activity by using a report analysis;

FIG. 4C is a Northern blot image illustrating the change in mRNA level of Mdm2, p53, p21 in case of Enigma overexpression;

FIGS. 4D & 4E are Western blot images illustrating that Enigma regulates Mdm2 level p53-independently and regulates protein levels of p53 and p21 regulation of p53 and p21 Mdm2-dependently;

FIGS. 5A & 5B Western blot images illustrating that an in-vivo binding between Enigma and Mdm2 occurs p53-independently and Enigma-p53 binding occurs Mdm2-dependently;

FIG. 5C is a Western blot image illustrating that an in-vitro binding between Enigma and Mdm2 occurs p53-independently and Enigma-p53 binding occurs Mdm2-dependently;

FIG. 5D is a schematic diagram and a Western blot image which indicate an Mdm2 domain (400-491 amino acids) which Enigma binds to;

FIGS. 5E & 5F are schematic diagrams and Western blot images which indicate that LIM3 domain of Enigma which Mdm2 binds to;

FIG. 5G is a schematic diagram illustrating the Enigma-Mdm2-p53 ternary complex;

FIGS. 7A & 7B are Western blot images illustrating when Enigma is overexpressed in cells, Mdm2's self-ubiquitination is inhibited and p53's ubiquitination is increased; when Enigma expression is inhibited, the event is reversed;

FIG. 7C is a Western blot image illustrating a LIM3 domain of Enigma binds to Mdm2 to inhibit Mdm2's self-ubiquitination;

FIG. 7D is a Western blot image illustrating Mdm2 increasingly ubiquitinates p53 by Enigma;

FIGS. 8A & 8B is to prove that Enigma has no effect on Mdmd2 ubiquitination by PCAF both in vitro and in vivo;

FIGS. 10A & 10B are Western blot images and RT-PCR images illustrating that serum increases Enigma expression following SRF induction at transcription level and thereby protein level of Mdm2 increases and protein level of p53 is decreased;

FIGS. 10C & 10D are Western blot images illustrating Mdm2 stabilization, which is induced by HGF, is dependent on SRF and Enigma;

FIG. 10E is a Western blot image illustrating the effect of HGF on the SRF-Enigma-Mdm2 pathway is dependent on an MAP kinase;

FIGS. 10F to 10H are Western blot images and RT-PCR images illustrating that the effect of HGF on the SRF-Enigma-Mdm2 pathway occurs in mice;

FIGS. 11A & 11B are Western blot images and RT-PCR images illustrating the effect of serum removal on the SRF-Enigma-Mdm2 pathway;

FIG. 13A is a Western blot image illustrating that SRF and Enigma proteins are co-expressed with Mdm2 in human liver and stomach cancer tissues;

FIG. 13B is an immunofluorescent staining of tumor tissues showing that Enigma is co-localized with Mdm2 at apical cytoplasm of human stomach and colorectal tumor cells.

FIGS. 14A & 14B are a cell count method and a crystal violet staining image showing that Enigma weakens adriamycin (ADR)-mediated cytotoxic effect p53-dependently and increase the cell viability;

FIG. 14C is a Western blot image illustrating the change in protein levels of Mdm2 and p53 according to the expression amount of Enigma in the presence of ADR;

FIGS. 15A & 15B show Enigma's effect on proliferation of cell lines where p53 is unexpressed;

FIGS. 15C & 15D are Western blot images and crystal violet staining images investigating protein levels of Mdm2 and p53 and cell viability in the condition above;

FIGS. 16A & 16B are graphs by a cell counting method and Western blot images showing that Enigma induces resistance to ADR in HLK3 hepatoma cell line, and chemo-resistance is increased when Enigma expression is increased;

FIGS. 16C & 16D are graphs by a cell counting method and Western blot images that show that Enigma confers chemo-resistance by regulating protein levels of Mdm2 and p53 in the presence of etoposide or nutlin3a;

FIGS. 16E & 16F are a graph and a mass image showing that resistance to ADR occurs when Enigma is overexpressed in mouse tumor model, and tumor growth is effectively inhibited when Enigma expression is inhibited;

FIG. 16G is a Western blot image illustrating the change in expression of Enigam-Mdm2-p53 in tumors excised from mice;

FIG. 17B illustrates an analysis result of cycle of an HLK cell in the condition of FIG. 16A.

DESCRIPTION OF THE PREFERRED EMBODIMENTS

Figure 6B:
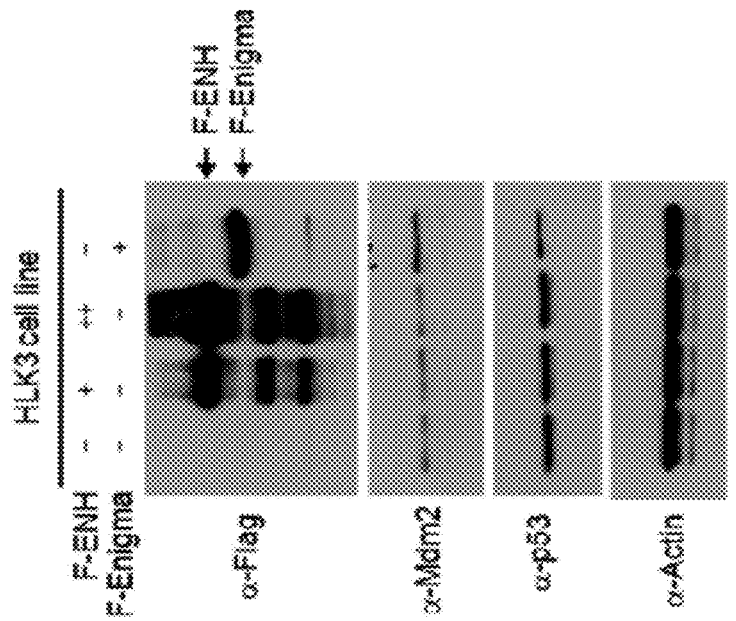
FIG. 6B is a Western blot image illustrating ENH has no effect on protein levels of Mdm2 and p53 in cells.

Features and advantages of the present invention will be more clearly understood by the following detailed description of the present preferred embodiments by reference to the accompanying drawings. It is first noted that terms or words used herein should be construed as meanings or concepts corresponding with the technical sprit of the present invention, based on the principle that the inventor can appropriately define the concepts of the terms to best describe his own invention. Also, it should be understood that detailed descriptions of well-known functions and structures related to the present invention will be omitted so as not to unnecessarily obscure the important point of the present invention.

The terms used herein are defined as below.

As used herein, the term "prevention" refers to all acts to inhibit the growth or transition of cancer by administering a composition of the present invention.

As used herein, the term "treatment" refers to all acts to improve or change beneficially cancer symptoms by administering a composition of the present invention.

As used herein, the term "administering" refers to providing a composition of the present invention for an individual by any suitable method.

As used herein, the term "individual" refers to all animals such as human, ape, dog, goat, pig or mouse, etc., with diseases for which a composition of the present invention is administered to possibly improve cancer symptoms.

As used herein, the term "pharmaceutically effective amount" refers to an amount sufficient for treatment as a reasonable benefit or risk ratio applicable to medical treatment, which may be determined from factors including type of cancer, severity, medication activity, sensitivity to medication, administering time, administering route and excretion ratio, treatment period, co-administering medication, and other well-known factors in the art.

The present invention is described in details as below.

The present invention provides a method of decreasing stability of Mdm2 and of increasing p53 activity by inhibiting Enigma expression or activity.

The present inventors identified that the stability of Mdm2 is regulated dependently on Enigma expression (See FIGS. 4A, 4D and 4E), and that, since Mdm2 is a E3 ligase with p53 as a substrate, the Mdm2 stabilization results in enhancing ubiquitination and degradation of p53, thereby ablating the antiproliferative activities of p53 (See FIGS. 4A to 4E), and that Enigma inhibits the self-ubiquitination of Mdm2, resulting in stabilization of Mdm2, and stimulates Mdm2-mediated ubiquitination of p53 (See FIGS. 7A to 7D).

Furthermore, the present inventors observed the function of Enigma in the cell proliferation inducing condition caused by growth promoting factor, to investigate the effects on cell growth by Enigma's regulation of Mdm2-p53 expression. Resultantly, revealed was that Enigma expression was enhanced by SRF and Enigma plays a role in assisting cell proliferation by stabilizing Mdm2 and destabilizing p53 (See FIGS. 9A to 9E and FIGS. 10A to 10E).

The inhibition of Enigma expression or activity of the present invention is preferred, but is not limited, to use those selected from the group consisting of substances of inhibiting transcription of an Enigma gene, substances of inhibiting translation of transcribed Enigma mRNA, or substances of inhibiting the function of an Enigma protein.

The transcription inhibitor is preferred, but is not limited, to use a promoter, an enhancer, a protein or compound binding to a transcription regulating factor which binds to a promoter.

A substance of inhibiting the translation of mRNA is preferred, but is not limited, to use a low-molecular-weight compound, RNA, siRNA or shRNA using an antisense nucleic acid sequence or RNAi technique.

Details for them will be specifically described below:

1) RNAi

RNA interference (RNAi) is a post-transcriptional gene silencing mechanism where degradation of a corresponding mRNA occurs by inducing a double-stranded RNA (dsRNA), which is corresponding to an Enigma gene, into a cell or organism. Since, by the RNAi effect, multiple cell divisions are maintained prior to a comeback of gene expression, RNAi is a very strong method of making a knockout or 'knockdown' which is aimed at the RNA level. It was observed that RNAi has been identified as successful in human cells including human embryonic kidney and HeLa cells (Elbashir et al. Nature 411, 494-498, 2001).

Standard methods in molecular biology are used for RNAi technology in gene silencing. dsRNA, which corresponds to the sequence of a target gene to be inactivated, may be produced by a standard method, for example, a double-stranded simultaneous transcription of template DNA using T7 RNA polymerase. A dsRNA production kit in use for RNAi may include commercially available products (for example, a product made by New England Biolabs, Inc.). Transfection methods of dsRNA and a processed plasmid for producing dsRNA are commonly known in the art.

2) siRNA siRNA refers to a short, and double-stranded RNA which may induce RNAi phenomenon by a cleavage of a specific mRNA.

siRNA is not limited to a perfectly-paired RNA portion in which two RNA strands pair up, and may include nonpairing portions due to mismatch (the corresponding bases are not complimentary), bulge (lacking in a base corresponding to one stand), etc. The length of a paired base is 10 to 40 base pairs, preferably 15 to 30 base pairs to disturb Enigma activity and expression. The terminal structure of siRNA may be either blunt terminus or a terminal overhang if siRNA can silence the target gene expression due to the RNAi effect. The cohesive terminal structure may include a 5' overhanging structure as well as a 3' overhanging structure. The number of overhanging bases is not limited. For example, the number may be 1 to 8 base pair(s), preferably 2 to 6 base pairs. The length of siRNA herein is that of paired polynucleotide. One end of siRNA may have a low-molecular-weight RNA (for example, a natural RNA molecule such as tRNA, rRNA, viral RNA, or an artificial RNA molecule) if the inhibitory effect on a target gene expression can be maintained. The terminal structure of siRNA does not necessarily have the cut off structure at both ends thereof, and may have a stem-loop structure in which an end of one strand of double-stranded RNA is connected by a linker RNA. There is no particular limitation in the length of the linker unless that length hinders the paring of the stem portion.

Disclosure on a method of designing and producing siRNA with known genes can be referred to the following documents, for example, [Chalk A M, Wahlestedt C, Sonnhammer E L. Improved and automated prediction of effective siRNA Biochem. Biophys. Res. Commun. 2004 Jun. 18; 319(1):264-74; Sioud M, Leirdal M., Potential design rules and enzymatic synthesis of siRNAs, Methods Mol. Biol. 2004; 252: 457-69]. Furthermore, to produce a modified and more stable siRNA, documents, e.g. [PCT Laid-Open Publication No. WO 2004/015107, U.S. Pat. Nos. 5,898,031 and 6,107,094] may be referred.

A DNA-containing vector has been developed, which can produce siRNA in cells. The method generally includes transcription of a short hairpin which is effectively processed to form siRNA in cells. The documents related to such method may be referred to: [Paddison et. al., PNAS 2002, 99:1443-1448; Paddison et. al., Genes & Dev 2002, 16:948-958; Sui et. al., PNAS 2002, 8:5515-5520; and Brummelkamp et. al., Science 2002, 296:550-553]. The documents describe methods for producing siRNA which specifically targets various endogenously and exogenously expressed genes. On delivery of siRNA, for example, the documents may be referred to: [Shen et. al., FEBS letters 539:111-114 (2003); Xia et. al., Nature Biotechnology 20:1006-1010 (2002); and Reigh et. al., Molecular Vision 9:210-216 (2003)]. siRNA was successfully used for inhibition in primate, and further detailed explanations may be referred to a document [Tolentino et. al., Retina 24(1) February 2004 pp 132-138].

On uses of siRNA as a therapeutic agent, for example, the following documents may be referred to: [Korean Patent Registration No. 10-0653738, Korean Patent Registration No. 10-0749859, Korean Patent Registration No. 10-0930282, and Korean Patent Registration No. 10-0810034].

3) Antisense Nucleic Acid Sequence

For nucleic acid encoding Enigma, antisense nucleic acid molecules may be used as an inhibitor. 'Antisense nucleic acid' includes nucleic acid sequence complementary to a 'sense nucleic acid' encoding Enigma, for example, complementary to a coding strand of a double-stranded cDNA or complementary to mRNA sequence. Thus, the antisense nucleic acid may form hydrogen bonds with the sense nucleic acid. The antisense nucleic acid may be complementary to the entire coding strand or its part (e.g. a coding region). Although the antisense nucleic acid molecule may be complementary to the entire coding region of an Enigma mRNA, antisense oligonucleotide is more preferable for only a part (e.g. a translation initiation portion) of the coding or non-coding region of the Enigma mRNA. Antisense oligonucleotide may be, for example, about 5 to 50 nt long. Antisense nucleic acid may be constructed by using chemical synthesis and enzyme linked reaction according to well-known methods. For example, it may be very easy to produce antisense nucleic acid using chemical synthesis method such as phosphoramidite chemistry of sulfurizing acetonitrile into tetraethylthiuram disulphide, which is disclosed in the document [Tetrahedron Lett. 32, 30005-30008, 1991]. Examples of a modified nucleotide in use for production of the antisense nucleic acid may be 5-fluorouracil, 5-bromouracil, 5-chlorouracil, 5-iodouracil, hypoxanthine, xanthine, 4-acetylcytosine, 5-(carboxyhydroxylmethyl)uracil, 1-methylinosine, 2,2-dimethylguanine, 2-methyladenine, 2-methyladenine, 2-methylguanine, 3-methylcytosine, 5-methylcytosine, N6-adenine, 5-carboxymethylaminomethyl-2-thiouridine, 3-(3-amino-3-N-2-carboxypropyl)uracil, 5'-methoxycarboxymethyluracil, 5-methoxyuracil, 2-methylthio-N-6-isopentenyladenine, 1-methylguanine, 7-methylguanine, 5-methylaminomethyluracil, 5-methoxyaminomethyl-2-thiouracil, beta-D-mannosylqueosine, 2-thiouracil, 4-thiouracil, 5-methyluracil, uracil-5-oxyacetic acid methylester, uracil-5-oxyacetic acid (v), 2,6-diaminopurine, 5-methyl-2-thiouracil, pseudouracil, queosine, 2-thiocytosine, 5-carboxymethylaminomethyluracil, dihydrouracil, beta-D-galactosylqueosine, inosine, N6-isopentenyladenine, 5-methyl-2-thiouracil, (acp3)w and wybutoxosine. As occasion arises, the antisense nucleic acid may be biologically generated by using expression vectors.

Although it is preferable that substances inhibiting function of the Enigma protein may include peptide binding to the protein, antibody, compound, peptide mimetics, etc., the present invention is not limited thereto.

Details for them will be specifically described below:

1) Peptide Mimetics

It is possible to inhibit an original Enigma polypeptide from binding to Mdm2 by producing mimetics (e.g. peptide or non-peptide pharmaceuticals), which inhibits a protein-binding domain of Enigma polypeptide (EU Patent Application EP 0412765 and EP 0031080).

Main residues of a non-hydrolyzed peptide analog may be generated by using 13-turn dipeptide core (Nagai et al. Tetrahedron Lett 26:647, 1985), keto-methylene pseudopeptide analogs (Ewenson et al. J Med Chem 29:295, 1986; and Ewenson et al. in Peptides: Structure and Function(Proceedings of the 9th American Peptide Symposium) Pierce Chemical Co. Rockland, Ill., 1985), azepine (Huffman et al. in Peptides: Chemistry and Biology, G. R. Marshall ed., ESCOM Publisher: Leiden, Netherlands, 1988), benzodiazepine (Freidinger et al. in Peptides; Chemistry and Biology, G. R. Marshall ed., ESCOM Publisher: Leiden, Netherlands, 1988), β-amino alcohol (Gordon et al. Biochem Biophys Res Commun 126:419 1985), and substituted gamma lactam ring (Garvey et al. in Peptides: Chemistry and Biology, G. R. Marshell ed., ESCOM Publisher: Leiden, Netherlands, 1988).

The present invention provides a method of producing Enigma-siRNA expression vector (siEnigma) to inhibit Enigma expression.

In specific, based on a method disclosed in Korean Patent Registration No. 877824 (U. S. patent application Ser. No. 12/093093(May 08, 2008)), a recombinant vector was produced as it is complementary to mRNA of Enigma, preferably is indicated as SEQ ID NO: 2 or SEQ ID NO: 5 (5'-AAA-GACCTTCTACTCCAAGAA-3' or 5'-AATGCCATGGCT-GTGACTTCA-3', respectively), and cloned into a pSuper plasmid vector to be expressed by an H1 promoter. Also, an Enigma-siRNA expression vector for adenovirus production was prepared, which contains an H1 promoter, Enigma-siRNA, and even five T bases ($T_5$) of transcription termination sequences, by processing the pSuper plasmid vector with a restriction enzyme into a pShuttle vector for adenovirus production that allows genes to be transferred and expressed into a cell. Additionally, after Enigma was cloned into a pCMV-Taq2b vector such that the mRNA of Enigma was expressed by a CMV promoter, and thereafter adenovirus F-Enigma was produced to allows Enigma to be transferred into a cell (see FIGS. 1 to 3, and U. S. patent application ser. No. (May 08, 2008) 12/093,093; Korean Patent Registration No. 877824).

Also, the present invention provides an anti-cancer composition or an anti-cancer adjuvant, which includes an Enigma expression inhibitor or an Enigma activity inhibitor as an effective ingredient.

The Enigma expression inhibitor may be selected from the group consisting of antisense oligonucleotide complimentarily binding to mRNA of an Enigma gene, short interfering RNA, short hairpin RNA, and RNAi, however, the present invention is not limited thereto.

The Enigma activity inhibitor may be selected from the group consisting of compound complimentarily binding to an Enigma protein, peptide, peptide mimetics, and antibody, however, the present invention is not limited thereto.

The cancer may be selected from the group consisting of stomach cancer, liver cancer, and colon cancer, however, the present invention is not limited thereto.

The present inventors found out that Enigma is co-expressed with Mdm2 in various type of cancer tissues (see FIGS. 13A and 13B), that Enigma overexpression in cancer cells induces resistance to anti-cancer agents, and that the treatment of siEnigma inhibiting Enigma expression induces apoptosis of cancer cells effectively (see FIGS. 14A to 14D; FIGS. 16A to 16G; and FIG. 17). Thus, an Enigma expression inhibitor or an Enigma activity inhibitor may be usefully utilized as an effective ingredient for anti-cancer therapeutic agent by efficiently inducing apoptosis of cancer cells, and may be usefully utilized as an effective ingredient for anti-cancer adjuvant by inhibiting resistance to anti-cancer agents.

The anti-cancer composition or anti-cancer adjuvant of the present invention includes 0.0001 to 50% by weight of the effective ingredient relative to the total weight of the composition.

The anti-cancer composition or anti-cancer adjuvant of the present invention may include one or more type of other effective ingredient(s) showing an identical or similar function in addition to the effective ingredient.

The anti-cancer composition or anti-cancer adjuvant of the present may be produced containing one or more type of a pharmaceutically acceptable carrier(s) in addition to the effective ingredient described above. As the pharmaceutically acceptable carrier, saline solution, sterilized water, linger's solution, buffer saline, dextrose solution, maltodextrin solution, glycerol, ethanol, liposome, and at least one combination thereof, may be used, and if necessary, other typical additives such as antioxidants, buffer solution, bacteriostatic agents, etc., may be added. Moreover, it can be formulated in the form of an injectable formulation such as aqueous solution, suspension and emulsion, a pill, a capsule, a granule, or a tablet by supplementarily adding diluent, dispersing agent, surfactant, binder and lubricant. And it may be used combining a target-specific antibody or other ligands with the carrier to act specifically upon a target organ. Furthermore, it is possible to preferably formulize according to each disease or ingredients using a suitable method in the art, for example, a method disclosed in Remington's Pharmaceutical Science (the latest edition), Mack Publishing Company, Easton Pa.).

Further, the present invention provides a method of treating cancer, including administrating an Enigma expression inhibitor or an Enigma activity inhibitor in a pharmaceutically effective amount to an individual suffering from cancer.

The Enigma expression inhibitor may be selected from the group consisting of antisense oligonucleotide complimentarily binding to mRNA of an Enigma gene, short interfering RNA, short hairpin RNA, and RNAi, however, the present invention is not limited thereto.

The Enigma expression inhibitor may be selected from the group consisting of compound complimentarily binding to an Enigma protein, peptide, peptide mimetics, and antibody, however, the present invention is not limited thereto.

The cancer may be selected from the group consisting of stomach cancer, liver cancer, and colon cancer, however, the present invention is not limited thereto.

The administering method is not particularly limited, and thus it may be a parenteral administering (for example, applied intravenously, subcutaneously, intraperitoneally, or locally) or oral administering. Although it is preferable to administer parenterally, more preferable to administer subcutaneously, the present invention is not limited thereto.

The range of dosage varies according to a patient's body weight, age, sex, health status, diet, dose time, dose method, excretion rate, the severity of disease, etc. The daily dosage for a compound is in the range of about 0.1 to 100 mg/kg, preferably 0.5 to 10 mg/kg. It is preferable to administer the formulation one or more times a day, however, the present invention is not limited thereto.

The present inventors observed that Enigma is co-expressed with Mdm2 in various types of cancer tissues, that Enigma overexpression in cancer cells induces resistance to anti-cancer agents, and that the treatment of siEnigma inhibiting Enigma expression induces effective apoptosis of cancer cells. Consequently, the present inventors found out that an Enigma expression inhibitor or an Enigma activity inhibitor may be used as an effective ingredient for anti-cancer therapeutic agent by inducing effective apoptosis of cancer cells.

Also, the present invention provides a method of screening candidate substances for anti-cancer agents, which uses an Enigma-dependent expression level of Mdm2 or p53. In the present invention, since Mdm2 expression is increased due to its stabilization depending on Enigma expression and P53 expression is decreased via the Mdm2, it is possible to screen a substance having anti-cancer activity by selecting a substance that allows the expression of the Enigma or Mdm2 to be decreased or the expression level of p53 to be increased.

In particular, the screening method may include:
1) treating candidate substances on cells expressing Enigma and Mdm2;
2) measuring a binding level for Enigma and Mdm2; and
3) selecting candidate substances to decrease the binding level for Enigma and Mdm2, compared to a control group untreated with candidate substances. However, the present invention is not limited to the above.

Furthermore, the screening method may include:
1) treating candidate substances on cells expressing Enigma, Mdm2 and p53;
2) measuring a binding level for Enigma and Mdm2; and
3) selecting candidate substances to decrease the binding level for Enigma and Mdm2, compared to a control group untreated with candidate substances. However, the present invention is not limited to the above.

A candidate substance as set forth in the screening method may be selected from the group consisting of a nucleic acid, a protein, other extracts, a compound and a natural substance, however, the present invention is not limited to the above.

An expression level as set forth in the screening method may be measured by measuring the transcriptional activity level of genes or by measuring the amount of expressed proteins, however, the present invention is not limited to the above.

The transcriptional activity level may be measured through Luciferase Assay and the amount of proteins may be measured through Western blot, however, the present invention is not limited to the above.

Furthermore, the present invention provides a method of screening an anti-cancer composition, using a binding level for Enigma and Mdm2.

The present inventors identified that Enigma and Mdm2 interacts directly, and Enigma and p53 interacts indirectly via Mdm2 (see FIGS. 5A to 5C). Also, the present inventors identified that the LIM3 portion of Enigma interacts with 401 to 491 (a RING domain portion) of Mdm2 (see FIGS. 5D to 5G). Thus, it can be understood that substance inhibiting an interaction between Enigma and Mdm2 may become anti-cancer active by weakening the stabilization of Mdm2 and activating p53.

The screening method may include:
1) contacting Enigma and Mdm2 in the presence or absence of candidate substances;
2) measuring a binding level for Enigma and Mdm2; and
3) selecting candidate substances to decrease the binding level for Enigma and Mdm2, compared to the absence of candidate substances. However, the present invention is not limited to the above.

Furthermore, the screening method may include:
1) bringing cells expressing Enigma and Mdm2 into contact with candidate substances;
2) measuring a binding level for Enigma and Mdm2; and
3) selecting candidate substances to decrease the binding level for Enigma and Mdm2, compared to a control group untreated with candidate substances. However, the present invention is not limited to the above.

A candidate substance as set forth in the screening method may be selected from the group consisting of a nucleic acid, a protein, other extracts, a compound and a natural substance, however, the present invention is not limited to the above.

Binding as set forth in the screening method may be measured by an immunoprecipitation method. Immunoprecipitation, for example, may be performed by a method in a document (Harlow and Lane, *Antibodies*, 511-52, Cold Spring Harbor Laboratory publications, New York, 1988). SDS-PAGE is generally used for analysis of immunoprecipitated proteins, and binding proteins may be analyzed by the molecular weight of proteins using gel of a suitable concentration.

As set forth in the screening method, a two-hybrid system, which uses cells, may be employed ("MATCHMAKER Two-Hybrid system", "MATCHMAKER Mammalian Two-Hybrid Assay Kit", "MATCHMAKER one-Hybrid system" (Clontech); "HybriZAP Two-Hybrid Vector System" (Stratagene); Reference: Dalton and Treisman, *Cell* 68: 597-612, 1992; Fields and Stemglanz, *Trends Genet.* 10: 286-92, 1994).

In the screening method, a biosensor using surface plasmon resonance phenomenon may be used as a means of detecting or quantifying substances bound in the present invention. In use of the biosensor, interaction by the binding may be observed real-time as a surface plasmon resonance signal.

The present invention provides a method of diagnosing cancer, identifying treatment results, or assessing prognosis, the method including measuring an Enigma expression level in cancer cells, using one or more of antibody reactive with Enigma and nucleic acid complementary to Enigma genes.

Furthermore, the present invention provides a kit in use for diagnosing cancers, including one or more of antibody reactive with Enigma and nucleic acid complementary to Enigma genes.

Figure 17A:
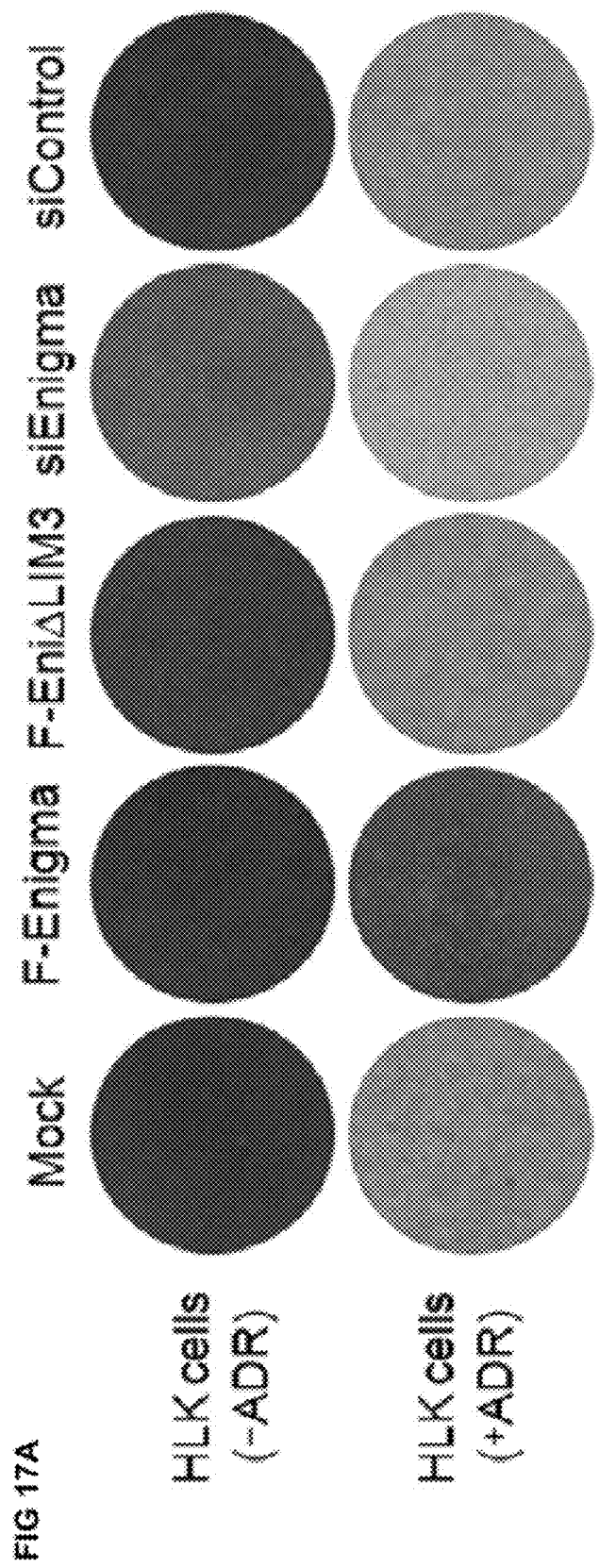
FIG. 17A is a crystal violet staining image of an HLK cell in the condition of FIG. 16A.

The present inventors observed Enigma overexpression in cancer cells, and resultantly confirmed that SRF and Enigma were co-expressed with Mdm2 in human liver and stomach cancer cells (see FIGS. 13A to 13B). Also, the present inventors found out that cancer cells' growth and resistance to anti-cancer agents were induced dependently on p53 and an Enigma expression level in cancer cells (see FIGS. 14A to 14D; FIGS. 16A to 16G; FIG. 17). Therefore, measuring the level of Enigma expression make it possible to know the extent of apoptosis of medicaments relative to cancer cells in cancer therapy, and thus may be used as a method of assessing the prognosis of anti-cancer therapy.

In the method of diagnosing cancers, detection of Enigma expression level higher than a normal range tells that a patient is suffering from cancer. Furthermore, in a diagnosis reagent of an individual who has undergone or is undergoing cancer therapy, detection of Enigma expression level in the normal range tells a success of cancer therapy, and detection of Enigma expression higher than the normal range in the diagnosis reagent tells that the cancer therapy should continue to be applied. Furthermore, in a diagnosis reagent of an individual who is suffering from cancer, detection of normal Enigma expression level in the normal range tells the prognosis is good, however, detection of Enigma expression level higher than the normal range in the diagnosis reagent tells that the prognosis is bad.

A kit of the present invention in use for diagnosing cancers may include one or more substance, which is reactive to Enigma, and a reagent for detecting reaction product and instructions related thereto. For example, one or more substance which is reactive to Enigma may be an RNA or DNA complementary to RNA or DNA of Enigma, and an antibody which binds to an Enigma protein. A reagent for detecting reaction product may be a nucleic acid, a protein marker and a color reagent.

The present invention also provides a use for utilizing an Enigma expression inhibitor or an Enigma activity inhibitor for preparation of an anti-cancer composition.

The present invention also provides a use for utilizing an Enigma expression inhibitor or an Enigma activity inhibitor for preparation of an anti-cancer adjuvant.

The present invention also provides a use for utilizing an Enigma expression inhibitor or an Enigma activity inhibitor for manufacturing a kit in use for diagnosing cancers, identifying therapeutic results, or assessing prognosis.

The Enigma expression inhibitor may be selected from the group consisting of antisense oligonucleotide complimentarily binding to mRNA of an Enigma gene, short interfering RNA, short hairpin RNA, and RNAi, however, the present invention is not limited thereto.

The Enigma activity inhibitor may be selected from the group consisting of substance complimentarily binding to an Enigma protein, peptide, peptide mimetics, antibody, and compound, however, the present invention is not limited thereto.

The cancer may be selected from the group consisting of stomach cancer, liver cancer, and colon cancer, however, the present invention is not limited thereto.

The present inventors observed that Enigma is co-expressed with Mdm2 in various types of cancer tissues, that Enigma overexpression in cancer cells induces resistance to anti-cancer agents, and that the treatment of siEnigma inhibiting Enigma expression induces effective apoptosis of cancer cells. Consequently, the present inventors found out that an Enigma expression inhibitor or an Enigma activity inhibitor may be used as an effective ingredient for anti-cancer therapeutic agent by inducing effective apoptosis of cancer cells, and may be used as an effective ingredient for anti-cancer adjuvant by inhibiting resistance to anti-cancer agents.

Herebelow examples of the present invention will be described in details.

The examples below exemplify only the present invention, and thus it should be construed that the present invention is not limited to the examples below.

EXAMPLE 1

MDM2 Stabilization by Enigma and p53 Degradation Thereby

The present inventors cloned fragments obtained by a common PCR method into pCMV Taq2B (Stratagene, USA) to thereby produce a vector which overexpresses Enigma, by using a vector containing Enigma cDNA (SEQ ID NO: 1), which was furnished by Korea Research Institute of Bioscience and Biotechnology (KRIBB) as a template. Furthermore, the present inventors cloned a nucleotide fragment of 5'-AAAGACCTTCTACTCCAAGAA-3' SEQ ID NO: 2) that inhibits Enigma expression specifically into on the Hind III/Bgl II sites of pSuper plasmid vector (FIG. 2). Also, for easy introduction into a cell, adenovirus, containing siEnigma (FIG. 3), and adenovirus containing Flag-Enigma (FIG. 2) were produced in following manner, based on the method described in Korean Patent Registration No. 627377 (Hepatology 43, 1042-1052, 2006) and 877824 (U. S. patent application Ser. No. 12/093,093(May 08, 2008); Nat Med 12, 809-816, 2006).

The pSuper Enigma-siRNA plasmid prepared in advance was processed into pShuttle (BD Bioscience, USA) vector for adenovirus production with VbaI/HindIII, and then a DNA fragment containing $T_5$ transcriptional termination sequence was cloned at H1 promoter (pShuttle/Enigma-siRNA). To prepare adenovirus expressing F-Enigma, only an Enigma portion was cut from the prepared pCMV taq2B-Enigma with NotI/XhoI and by then cloned into a pCMV shuttle vector. A recombination of pAdEasy-1, which includes adenovirus genome, with pShuttle/Enigma-siRNA and pCMVshuttle-F-Enigma was performed by being simultaneously transduced to *E. coli* strain BJ5183. A plasmid containing recombinant adenovirus genome, which was obtained by homologous recombination in the *E. coli*, was identified through restriction enzyme analysis after separating DNA from an *E. coli* colony grown in Kanamycin selective medium.

Production of adenovirus particles in a plasmid containing recombinant adenovirus genome was performed as below. A plasmid containing recombinant adenovirus genome was cut with PacI so that terminal repeat (TR), a replication origin of adenovirus, is located at both ends of linearized DNA, and was transfected into an HEK293 cell (ATCC), which was grown in 60-mm culture plate by 70-80% confluency, using a calcium phosphate method. A plasmid containing recombinant adenovirus genome was introduced. Cells which generate adenovirus particles became cytopathic after 2-3 days, and formed plaques after 4-5 days. Cells which became cytopathic were collected and were froze-and-thawed, thereby releasing adenoviruses from the cells. Supernatants of the cell lysates were obtained by centrifugation. Cells, which were prepared in a 100-mm culture plate by 60-70% confluency, were infected with the supernatant of the cell lysates. Once cells die by proliferation after infection of adenovirus, the cells were recollected and then repeated the above procedure to create correct recombinant adenovirus. The number of viruses was determined by the plaque-forming method.

<1-1> Enigma Stabilizes Mdm2

Enigma's effect on ubiquitin-proteasome-dependent proteolysis of Mdm2 was identified by the following method: A Flag-Enigma expression vector was induced into an HLK3 cell line (Chonbuk National University Medical School, South Korea) concentration-wise (+: 2 μg, ++: 5 μg). Protein levels of Enigma and Mdm2 were determined by Western blotting after collecting cells in the presence or absence of MG132 (10 μM) for 12 hours. As a result, while Mdm2 protein level was elevated dependently on Enigma expression, protein levels of p53 and p21 decreased (FIG. 4A).

<1-2> p53 Protein Level Reflects p53 Activity

To identify whether a decrease in p53 protein level by Enigma leads to a decrease in p53 activity, activity of target gene promoters regulated by p53 was examined. After reporter genes (0.5 μg) such as p53RE-Luc, Bax-Luc, p21-Luc were introduced into HLK3 cell line, or $p53^{+/+}$ or $p53^{-/-}$ colon cancer cell line (HCT116, ATCC) concentration-wise with Flag-Enigma (+: 2 μg, ++: 5 μg) respectively, and the cells were treated or not treated with MG132 (10 μM) for 12 hours, a reporter assay (Promega, USA) on collected cells was performed. As the result, transcriptional activity of target genes regulated by p53 was shown to be inhibited concentration-dependently on Enigma expression (FIG. 4B).

<1-3> Enigma's Effect on mRNA Levels of Mdm2, p53, and p21

A Northern blotting was performed to test whether an expression change in Mdmd2 and p53 by Enigma occurred at the level of mRNA. A Flag-Enigma expression vector was transfected into an HLK3 cell line at two different doses (+: 2 μg, ++5 μg). Total RNA was extracted with RNeasy kit (Qiagen) after 48 hours, and a Northern blotting was performed with each probe (P1/P2 Mdm2, p53, p21). As the result, the amount of mRNA in P1-Mdm2, p53, and p21 was unvaried irrespective of the amount of Enigma expression, and the amount of mRNA in P2-Mdm2, which is regulated by p53, decreased dependently on Enigma expression (FIG. 4C). The result suggests that Enigma regulates Mdm2 and p53 levels at the post-transcriptional step.

<1-4> Enigma regulates p53 level Mdm2-dependently $Mdm2^{-/-}p53^{-/-}$ MEF and $Mdm2^{+/+}p53^{-/-}$ MEF cell lines (G. Lozano, M. D. ANDERSON CANCER CENTER) were used to identify whether an expression inhibition of p53 and p21 by Enigma is Mdm2-dependent. At 16 hours after an adenovirus vector (Ad-p53) was infected into each of said cell lines, Ad-F-Enimga (50 MOI), Ad-LacZ (50 MOI), Ad-siEnigma (100 MOI), Ad-siControl (100 MOI) were infected again. After 32 hours, the cells were collected, and a change in expression for each protein was identified by a Western blotting. As the result, expression of p53 and p21 decreased dependently on Mdm2 expression (FIG. 4D).

<1-5> Enigma Regulates p21 Level p53-Dependently $p53^{+/+}$, $p53^{-/-}$ cell lines were used to identify whether expression inhibition of p21 by Enigma is by way of p53 or not. Flag-Enigma, siEnigma were introduced to the $p53^{+/+}$, p53 cell lines. After 48 hours, protein levels of p53 and p21 were identified by a Western blotting. As the result, a change in p21 is caused by a change in p53, and a direct effect by Enigma was not shown (FIG. 4E).

EXAMPLE 2

Identification of an Enigma-Mdm2-p53 Ternary Complex

The present inventors, to test interaction between Enigma and Mdm2, generated mutants (F-PDZ, F-PDZ-LIM1, F-LIM) of Enigma in pCMVtaq2B vector by a common PCR cloning method, and produced mutants (GST-1-100, GST-101-491, GST-201-491, GST-301-491) of Mdm2 in pEBG vector by a PCR cloning method. His-Mdm2, Enigma, GST-p53, EniΔLIM3 proteins were respectively separated and purified from E. coli to identify the interaction in vitro.

<2-1> Enigma Interacts with p53 Through Mdm2 in Cells

Interaction between Enigma and Mdm2-p53 was identified by an IP method in a colon cancer cell line (HCT116) of $p53^{+/+}$ or $p53^{-/-}$ and $Mdm2^{-/-}p53^{-/-}$ MEF and $Mdm2^{+/+}$ MEF cell lines. As the result, interaction between Enigma and Mdm2 occurred irrespectively of p53, and in the presence of Mdm2, an Enigma-Mdm2-p53 complex was found to be formed (FIGS. 5A and 5B).

<2-2> Enigma Interacts with p53 Through Mdm2 In Vitro

In vitro binding assay was performed to identify directly in-vitro interaction between respective proteins (1 μg His-Mdm2, 0.5 μg Enigma, 1 μg GST-p53) which are separated and purified from E. coli. Binding between respective proteins were induced after mixing, the bindings between proteins were identified by a GST pull-down and an IP method. As the result, Enigma bound to Mdm2 directly, and bound to p53 when Mdm2 was present (FIG. 5C).

<2-3> Determination of a Binding Site Between Enigma and Mdm2

A binding site was determined by using respective mutants produced from Enigma and Mdm2. First, each mutant vector (5 μg) was introduced into a 293 cell line where Hag-Enigma is constitutively expressed, and afterwards binding was identified by GST pull-down and by a Western blotting with a Hag antibody (FIG. 5D). Also, each Enigma mutant (5 μg) and GST-Mdm2 expression vector (5 μg) were introduced into a 293T cell line (ATCC) by a calcium phosphate method. At 24 hours, the cells were collected, and binding was identified by IP with a Flag antibody and by a Western blotting with a GST antibody (FIG. 5E). Bacterially expressed EniΔLIM3, in which the LIM3 domain of Enigma was removed, were not bound to Mdm2 (FIG. 5C), and Mdm2 (401-491) and LIM3 domain of Enigma were shown as binding site. By identifying interaction between a GST-LIM3 mutant, which includes a LIM3 site only, and Mdm2 after an induction of cell lines by GST pull-down and by a Western blotting with an Mdm2 antibody, the present inventors could identify that the LIM3 site of Enigma binds to 401-491 site of Mdm2 (FIG. 5F). Thus, based on known Mdm2-p53 interaction, shown is that a "C" terminus of Enigma and a "C" terminus of Mdm2 are bound directly, with the binding structure of a "N" terminus of Mdm2 and a "N" terminus of p53 revealed (FIG. 5G).

<2-4> Enigma binds to Mdm2 Specifically

Figure 6A:
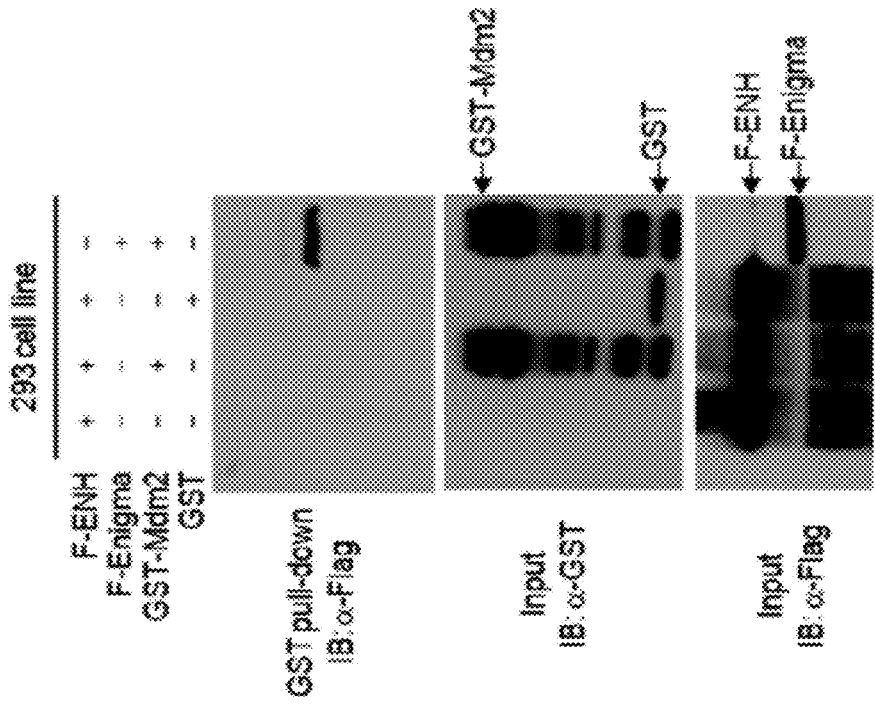
FIG. 6A is a Western blot image illustrating Enigma homolog (ENHk) does not bind to mdm2.

A binding between ENH (Enigma homolog), which retains a molecular structure similar to Enigma, and Mdm2 was tested. Expression vectors such as Flag-ENH, Flag-Enigma and GST-Mdm2 were transfected into a 293T cell line by a calcium phosphate method. After 48 hours when the cells were collected, GST pull-down and a Western blotting with a Flag antibody were performed. As the result, no binding between Mdm2 and ENH occurred (FIG. 6A). Furthermore, after an F-ENH expression vector was transfected into an HLK3 cell line concentration-wise (2, 5 μg), no expression change in Mdm2 and p53 was identified. As the result, ENH had no effect on the amount of expression in Mdm2 and p53 (FIG. 6B). Thus, the binding between Enigma and Mdm2 and the increase in Mdm2 expression thereby could be identified as specific interaction.

EXAMPLE 3

Enigma's Effect on Self-Ubiquitination of Mdm2 and Ubiquitination of p53

The present inventors tested Enigma's effect on self-ubiquitination of Mdm2 and ubiquitination of p53 in vivo and in vitro to elucidate a mechanism where Enigma binds directly to Mdm2 to stabilize Mdm2, and Mdm2 enhances degradation of p53.

<3-1> Enigma's In Vivo Effect on Ubiquitination of Mdm2 and p53

Flag-Enigma (5, 10 μg), siEnigma (10μ, 15 μg) were induced into an HLK3 cell line concentration-wise and treated with MG132 12 hours before their collection. His-Ub (5 μg) and F-Enigma (5, 10 μg) were induced into another 293T cell line concentration-wise and treated with MG132 12 hours before their collection. Cell protein extract was prepared with a lysis solution, and IP was performed with respective antibodies; a fluctuation in Mdm2-Ub and p53-Ub conjugates was identified by a Western blotting with Ub and His antibodies. As the result, the more overexpressed Enigma was in a cell, the more decreased Mdm2 ubiquitination was, the more increased p53 ubiquitination was; the more inhibited Enigma expression was, the more increased Mdm2 ubiquitination was, the more decreased p53 ubiquitination was (FIGS. 7A and 7B).

<3-2> Enigma Inhibits Self-Ubiquitination of Mdm2 and Promotes Ubiquitination of p53

In vitro ubiquitination assay was performed to test self-ubiquitination of Mdm2 by Enigma's binding. After ubiquitin reaction mixture (including E1, E2, His-Ub, ATP) was added and reacted to His-Mdm2 protein (0.5 μg), His-Mdm2 (C464A: 0.5 μg), Enigma protein (0.5, 1 μg), F-EniΔLIM3 (1 μg), a change in self-ubiquitination and binding proteins for Mdm2 were identified by an IP/IB method. As the result, self-ubiquitination of Mdm2 was inhibited by F-Enigma, which binds to Mdm2, and Enigma had no effect on an Mdm2 (C464A) variant where 464-cysteine on the Mdm2 RING finger region was substituted by alanine (FIG. 7C). Also, Enigma stimulated Mdm2-mediated p53 ubiquitination in vitro (FIG. 7D). Thus, Enigma was identified as a determining factor that shifts specificity of Mdm2 E3 ligase from itself toward p53.

<3-3> Enigma's Effect on PCAF-Mediated Mdm2 Ubiquitination

PCAF (p300-CBP-associated factor) induces the ubiquitination of Mdm2 (Nat Cell Biol 9, 331-338, 2007). When proteins purified from bacteria and described in FIG. 5-1a were used to perform an in-vitro ubiquitin experiment, Enigma had no effect on Mdm2 ubiquitination by PCAF (FIG. 8A). This event was also tested in an $Mdm2^{-/-}p53^{-/-}$ MEF cell line (FIG. 8B). The results suggest that Enigma inhibits specifically the self-ubiquitination of Mdm2 and enhances Mdm2-mediated ubiquitination of p53.

EXAMPLE 4

Identification of Factors that Activate an Enigma Promoter

Since p53 has a function to inhibit cell proliferation and Enigma induces Mdm2 stabilization in cells and causes protein level of p53 to decrease, whether an Enigma promoter is activated in a condition of cell proliferation and how the mechanism operates were investigated.

<4-1> Serum Activates an Enigma Promoter

Figures 9A, 9B, 9C, 9D, 9E, 9F:
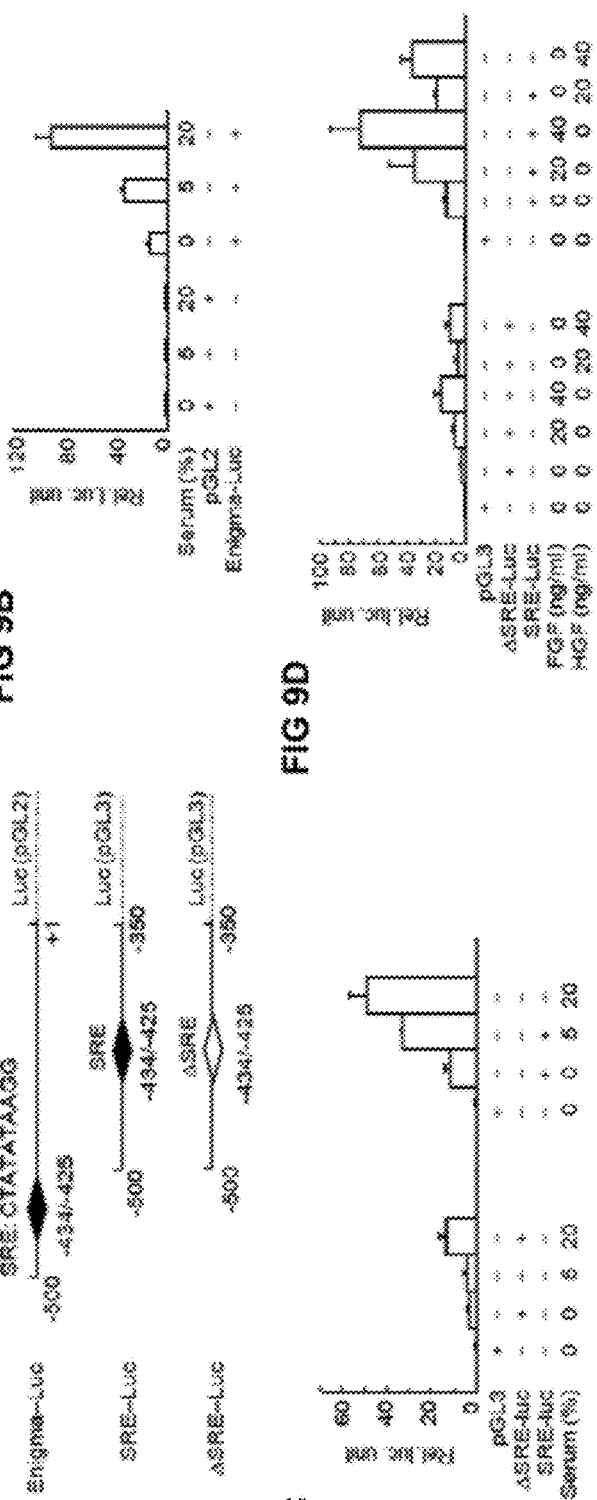
FIG. 9A is a schematic diagram of Enigma promoter-reporter constructs in which SRE is present or absent in the promoter region of Enigma.
FIG. 9B is a diagram which indicates that an Enigma promoter is activated by serum by using a report analysis.
FIGS. 9C & 9D are graphs showing that the SRE is essential for the serum-, FGF-, or HGF-mediated activation of Enigma promoter.
FIGS. 9E & 9F are the analytical results of EMSA and CHIP diagrams which indicate that SRF binds specifically to an SRE portion on an Enigma promoter.

The present inventors discovered that a serum response element (SRE) where a serum response factor (SRF) binds occurs on an Enigma promoter, and produced Enigma-Luc (pGL2), SRE-Luc, ΔSRE-Luc (pGL3) reporter vectors respectively, by inserting a fragment, which includes or does not include SRE in a promoter sequence, into a pGL2/3 vector with a luciferase (FIG. 9A). After Enigma-Luc was induced into an HLK3 cell line (0.5 µg), was cultured in DMEM with 0.1% PBS for 24 hours, and was cultured with 5% and 20% FBS added for 6 hours again, luciferase activity of collected cells were measured. As the result, activity of Enigma-Luc increased dependently on the concentration of serum (FIG. 9B).

<4-2> Growth Factors Activate Enigma Promoter through SRE

After SRE-Luc (0.5 µg), ΔSRE-Luc (0.5 µg), which were produced to test SRF dependence of Enigma expression, were induced into an HLK3 cell line, the cells were cultured in DMEM with 0.1% FBS for 24 hours, and were cultured with 5% and 20% FBS, FGF (20, 40 ng/ml), or HGF (20, 40 ng/ml) added for 6 hours again, luciferase activity of collected cells were measured. As the result, the reporter activity of SRE-Luc but not ΔSRE-Luc increased dependently on the concentration of growth factor (FIGS. 9C and 9D).

<4-3> SRF Binds to an SRE Site of an Enigma Promoter

EMSA and in vivo ChIP analyses were performed to test whether SRF binds specifically to an SRE site [5'-CTATATAAGG-3'(SEQ ID NO: 3)] of an Enigma promoter. The present inventors, to perform the EMSA analysis, produced a nucleoprotein extract of HLK3, which was treated or not treated with serum, brought the extract into reaction with an $^{32}$P-radiolabeled SRE nucleotide (5'-CTATATAAGG (SEQ ID NO: 3) X3), and then brought the reaction mixtures into reaction with an anti-SRF antibody, and identified the binding in a 6% acrylamide gel. As the result, revealed is that SRF binds specifically to the SRE site of Enigma promoter (FIG. 9E).

Furthermore, the present inventors, for ChIP analysis performed to identify whether SRF binds to an Enigma promoter in cells, fixed HLK3, which was treated or not treated with serum, with 1% formalin, and lysed collected cells by sonic treatment. The present inventors identified by PCR with a particular primer whether SRF binds to an SRE site of an Enigma promoter after obtaining an SRF-DNA complex going through IP with an anti-SRF antibody. As the result, revealed is that SRF binds to an SRE site of an Enigma promoter in cells (FIG. 9F). The results above suggest that in a condition of cell proliferation an Enigma promoter is activated by SRF and thereby the expression increases.

EXAMPLE 5

Serum or HGF Regulates SRF-Enigma-Mdm2-p53 Pathway

In a condition of cell proliferation or enhancing survival, an increase in Mdm2 has been reported (Growth factors 23, 183-192, 2005). The present inventors tested whether Enigma expression by SRF would stabilise Mdm2, and inhibit p53 in a cell and a mouse liver to identify if said event is caused by Enigma.

<5-1> Serum Regulates SRF-Enigma-Mdm2-p53 Pathway

The present inventors identified a change in protein by a Western blotting and a change in transcriptional level (mRNA) by RT-PCR, which uses total RNA separated condition-wise, respectively after culturing a $p53^{+/+}$ or $p53^{-/-}$ colon cancer cell line in a condition of removing serum, and again culturing the cell line in media containing 10% serum time-wise. As the result, revealed is that SRF increased from the transcriptional step, and therefore an amount of protein also increased, and an amount of protein in Enigma, which is transcriptionally activated, also increased. The increase in Enigma induced stabilization of Mdm2 protein and decreased protein level of p53. A series of increase in SRF-Enigma-Mdm2 was independent from p53 (FIGS. 10A and 10B).

Figures 11A, 11B:
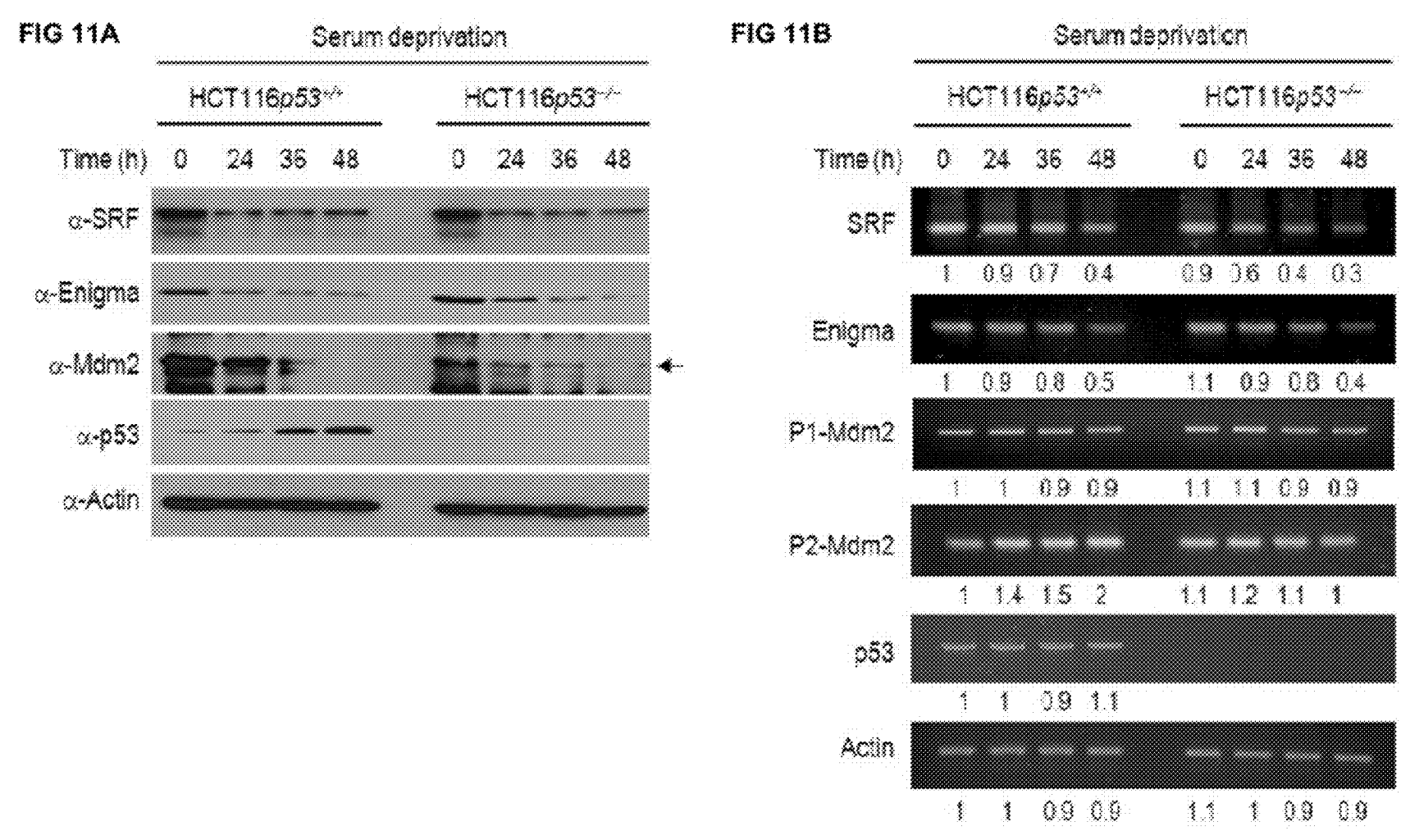

After culturing a $p53^{+/+}$ or $p53^{-/-}$ colon cancer cell line in media containing 10% serum, the present inventors identified, by a Western blotting and RT-PCR, changes in each molecule in a condition of removing serum time-wise. As the result, in a condition of restricted growth, mRNA and protein levels of SRF and Enigma are all decreased, protein level of Mdm2 decreased, and protein level of p53 increased (FIGS. 11A and 11B).

<5-2> HGF Regulates SRF-Enigma-Mdm2-p53 Pathway

The present inventors investigated whether SRF-Enigma-Mdm2 pathway is also regulated by HGF. The present inventors, to show specific relevance of SRF, Enigma, identified changes in each protein by a Western blotting after inducing 10 µg each of siEnigma, siSRF into an HLK3 cell line, culturing them in a condition of removing serum, and processing each with HGF (40, 60 ng/ml) 4 hours before cell collection. As the result, an increase in SRF-Enigma-Mdm2 and a SRF- or Enigma-dependent decrease in p53 were identified (FIG. 10C). Furthermore, the present inventors observed a change in Enigma and Mdm2 after directly inducing F-SRF into an HLK3 cell line concentration-wise (5, 10 µg). As the result, revealed is that SRF induced Enigma gene expression directly (FIG. 10D).

<5-3> An MAP Kinase Regulates SRF-Enigma-Mdm2 Pathway

Since an MAP kinase is known to be associated with SRF expression by cell growth factor (J Physiol Pharmacol 53, 147-157, 53, 2002), the present inventors hypothesized that an MAP kinase is associated with regulation of SRF-Enigma-Mdm2 pathway, and tested by using PD98059, MAP kinase-specific inhibitor. The present inventors treated the cells with HGF and with or without PD98059 after inducing Ad-p53 or Ad-LacZ into $Mdm2^{+/+}p53^{-/-}$ MEF cell lines. As the result, PD98059 abolished the HGF effect on SRF-Enigma-Mdm2 pathway (FIG. 10E).

Figure 12B:
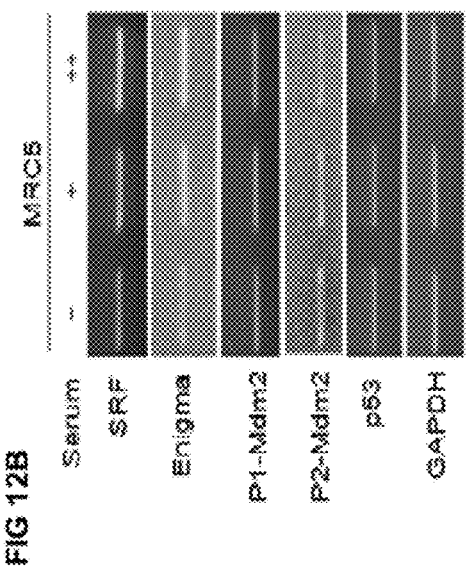
FIGS. 12A & 12B are Western blot images and RT-PCR images illustrating that the effect of serum on the SRF-Enigma-Mdm2 pathway occurs in human fibroblasts in a manner dependent on an MAP kinase.
Figure 12D:
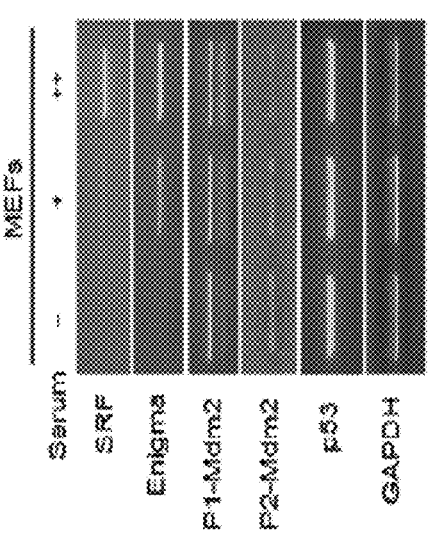
FIGS. 12C & 12D are Western blot images and RT-PCR images illustrating that the effect of serum on the SRF-Enigma-Mdm2 pathway occurs in mouse embryonic fibroblasts in a manner dependent on an MAP kinase.
Figure 12A:
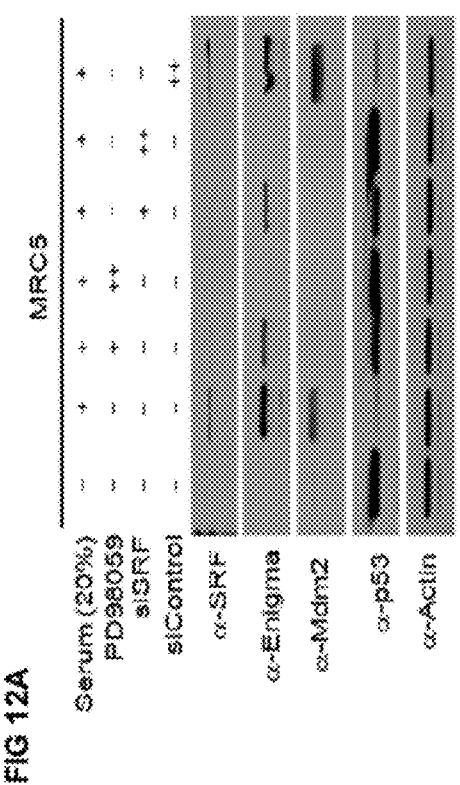
Figure 12C:
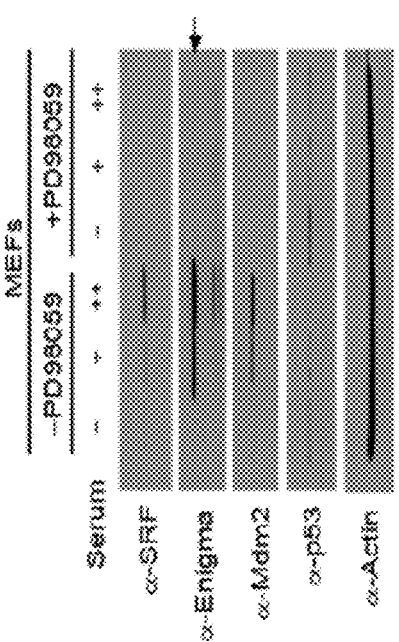

The present inventors identified serum response by using MRC5 (human normal fibroblast), MEF (mouse embryonic fibroblast) to identify presence of SRF-Enigma-Mdm2 pathway in normal cells. In case of MRC5, activity of SRF-Enigma-Mdm2 pathway by serum was inhibited when siSRF (10, 15 µg) is induced or PD98059 is present; in case of MEF, activity of SRF-Enigma-Mdm2 pathway was inhibited by PD98059 (FIGS. 12A and 12C). Thus, an amount of protein by transcriptional activity increased for SRF, Enigma, transcript level for Mdm2 (p1-Mdm2) and p53 was unvaried. However, transcript level for p2-Mdm2 changed dependently on an amount of p53 expression (FIGS. 12B and 12D). The results suggest that transcriptome of SRF-Enigma is primarily, orderly generated when a cell proliferates, and there is a pathway where Enigma protein stabilize Mdm2 and decrease p53.

<5-4> In Vivo Presence of SRF-Enigma-Mdm2-p53 Pathway

The present inventors identified a change in SRF-Enigma-Mdm2-p53 by a Western blotting after injecting each of Ad-p53 or Ad-LacZ virus (5×10$^8$ pfu) into tail vein of mice (Balb/c, Female, Taconic) and after 24 hours injecting HGF (100 µg/kg) into tail vein of mice again, removing livers time-wise. As the result, HGF induced protein expression by transcriptionally activating SRF, Enigma was induced by SRF at transcription level, and an amount of protein increased. According to an increase in Enigma, the amount of protein in Mdm2 increased and simultaneously that of p53 decreased (FIGS. 10F and 10G).

The present inventors, to observe a change in Mdm2-p53 according to a direct change in an amount of Enigma expression, identified an amount of each protein by a Western blotting after injecting or not injecting Ad-p53 into tail vein of mice (Balb/c, Female, Taconic) and after 24 hours injecting Ad-F-Enigma, Ad-LacZ, PBS into tail vein of mice again, removing livers after 48 hours. Furthermore, after injecting Ad-siEnigma, Ad-siControl and PBS into tail vein and injecting HGF into tail vein 8 hours before liver removal. As the result, if Enigma expression was high, Mdm2 was stabilized and p53 decreased; when Enigma expression was inhibited, Mdm2 stabilization by HGF was inhibited and p53 increased (FIG. 10H). The result suggests that SRF-Enigma-Mdm2-p53 is present in vivo.

EXAMPLE 6

SRF and Enigma are Co-Expressed with Mdm2 in Human Cancer Tissues

The present inventors, to identify whether in human cancer tissues (stomach cancer: Chungnam National University Medical School, South Korea; liver cancer: Chonbuk National University Medical School and Keimyung University Medical School, South Korea) induction of Enigma by SRF may cause Mdm2 stabilization and then induce an decrease in p53, lysed liver cancer tissues, stomach cancer tissues and corresponding normal tissues in tissue lysis buffer (Intron, Korea) and investigated them by a Western blotting. As the result, SRF and Enigma were co-expressed with Mdm2 in ten cases of liver and stomach tumors, where p53 was not detected (FIG. 13a, indicated by a single asterisk). Furthermore, in tissue array (available on the World Wide Web at tissuearray.com) planted in various types of human cancer tissues, Enigma-Mdm2 expression was observed by using an immuno-fluorescent staining method. As the result, Enigma is co-localized with Mdm2 at an apical region of cytoplasm in stomach cancer and colon cancer tissues (FIG. 13B). The result suggests that SRF-Enigma-Mdm2 is activated and p53 is likely attenuated in rapidly proliferating cancer cells.

Example 7

Enigma Promotes Cell Viability and Confers Chemo-Resistance

The present inventors investigated whether Enigma decreases protein level of p53, which induces apoptosis, and thereby increases cell survival ability and induces resistance to anti-cancer agents.

<7-1> p53-Dependent Induction of Apoptosis by Expression Inhibition of Enigma

Figure 14D:
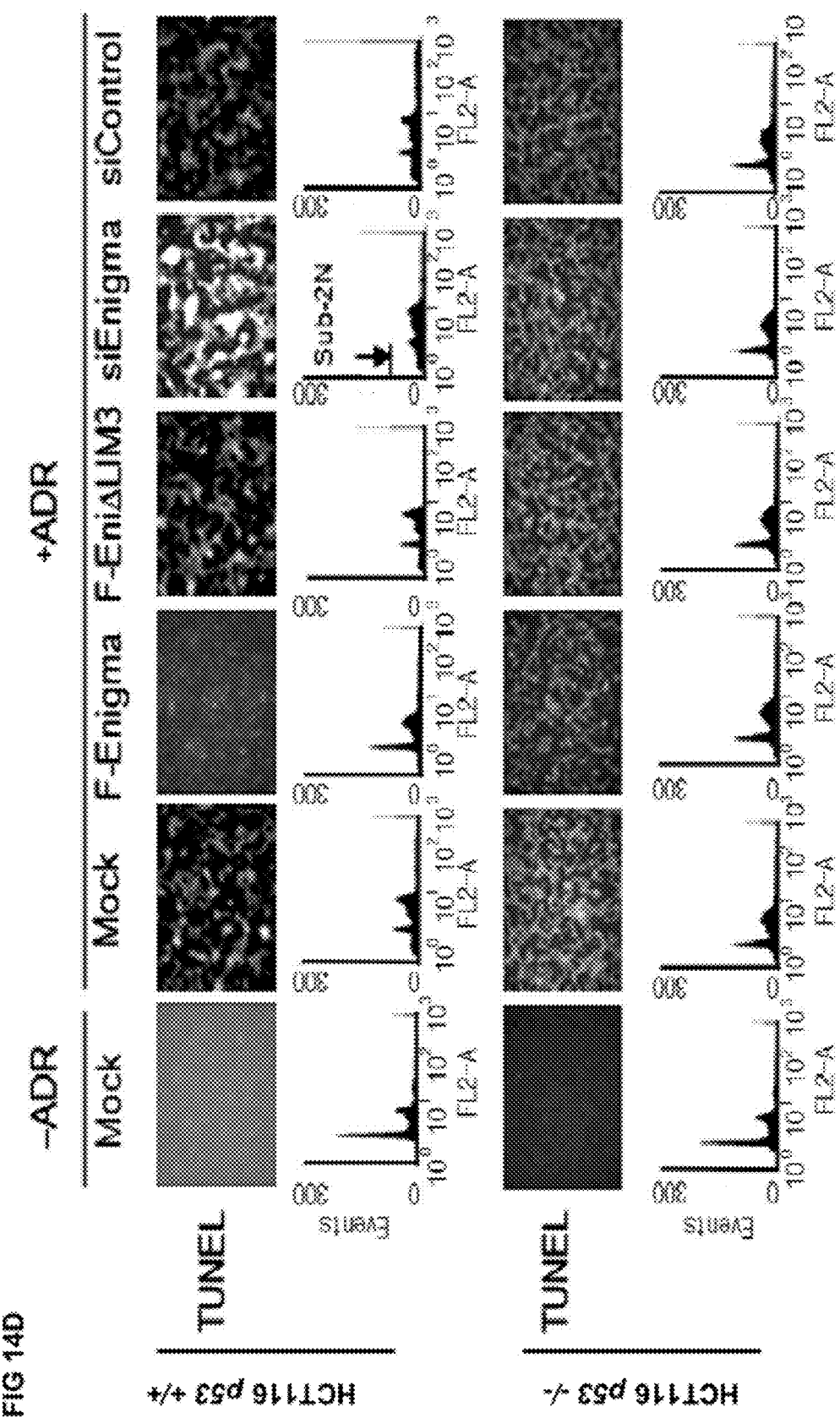
FIG. 14D is an image by a TUNEL method and a cell cycle analysis illustrating Enigma regulates cell viability p53-dependently in the presence of ADR.

The present inventors identified whether Enigma's effect on cell survival is p53-dependent by cell counting method and crystal violet method after inducing Flag-Enigma(5 µg) or siEnigma (10 µg) into HCT116 colon cancer cell lines of p53$^{+/+}$ or p53$^{-/-}$, and processing with adriamycin (ADR 20 µg/ml). As the result, cell's ability to survive increased in case of high Enigma expression in cells with wild-type p53 alone; in case of inhibited Enigma expression the cell's ability to survive decreased (FIGS. 14A and 14B). Furthermore, in H1299, H358, PC3, and Hep3B cell lines where p53 is not expressed an decrease in Enigma expression had little effect on the cell's ability to survive (FIG. 15). The present inventors tested whether Enigma's effect on cell survival is a regulation effect on apoptosis by the TUNEL method and cell cycle analysis. As the result, revealed is that in cell lines with wild-type p53 apoptosis by inhibition of Enigma expression was effective (FIG. 14D). Thus, found is that in the presence of ADR, an increasing effect by Enigma of the cell's ability to survive is mediated by p53 and caused by inhibition of inducing apoptosis.

Also, the present inventors, to identify a change in Enigma-Mdm2-p53 pathway in the presence of ADR, performed a Western blotting by processing ADR (2 µg/ml) under the same conditions above. As the result, irrespective of p53's presence, an decrease in Mdm2 by ADR was inhibited by overexpression of Enigma, and an increase or decrease in Mdm2-p53 was Enigma expression-dependent (FIG. 14C). Thus, found is that Enigma decreases p53 level via stabilization of Mdm2 and thereby promotes resistance of cancer cells to ADR.

EXAMPLE 8

Enigma Confers Chemo-Resistance In Vivo

The present inventors identified that p53-mediated apoptosis is regulated dependently on Enigma expression, and investigated whether ADR resistance is induced by Enigma in mouse xenograft model made of HLK3, a liver cancer cell line.

<8-1> Enigma's Effect on Tumor Cell Viability

The present inventors investigated cell viability by the cell counting method by introducing F-Enigma (5 µg) or siEnigma (10 µg) into an HLK3 cell line, untreated with ADR (20 µg/ml). As the result, in case of high Enigma expression, cell suicide by anti-cancer agents was inhibited; in case of inhibited Enigma expression, even in the absence of ADR, cell viability was effectively decreased (FIG. 16A and FIG. 17). The present inventors, to identify a change in Enigma-Mdm2-p53 pathway in process with ADR, performed a Western blotting in process with ADR (2 µg/ml) under the same conditions above. As the result, a chance in Mdm2-p53 expression was Enigma expression-dependent (FIG. 16B).

<8-2> Enigma Confers Resistance to Etoposide and Nutlin3a

Although etoposide (ETC) and nutlin3a (Sigma, USA) have distinct mechanisms, both are anti-cancer agents to activate p53 and thereby induce suicide of cancer cells (Science 303, 844-848, 2004). The present inventors tested whether Enigma enables cancer cells to show resistance to them. The present inventors identified a number of survived cells by the cell counting method by processing ETC and nutlin3a respectively in an HLK3 cell, where F-Enigma (5 µg) is induced. As the result, the present inventors identified that, in case of Enigma overexpression, resistance to ETC and nutlin3a was induced (FIG. 16C). The present inventors, to identify a change in Enigma-Mdm2-p53 pathway in process with ADR, performed a Western blotting in process with ADR (2 µg/ml) under the same conditions above. As the result, a chance in Mdm2-p53 expression was Enigma expression-dependent (FIG. 16B).

<8-3> Enigma Exhibits Resistance to ADR In Vivo

The present inventors, to test whether Enigma induces resistance of tumor cells to ADR in vivo, generated tumor on nude mice (Balb/c nu, Female, SLC, Japan). After first infecting Ad-F-Enigma (100 MOI), Ad-LacZ (100 MOI), Ad-siEnigma (200 MOI), Ad-siControl (200 MOI) into an HLK cell, the present inventors injected them into said mice (n=5/experimental group) subcutaneously. After 14 days when ADR (4 mg/kg) was injected into tail vein, the size of tumor was observed for 28 days. As the result, cancer cells where F-Enigma is expressed showed resistance to ADR, in proliferating similarly to control group untreated with ADR, and in a group where Enigma expression is inhibited, proliferation of cancer cells is most inhibited (FIGS. 16E and 16F). The present inventors, to identify an expression change in Mdm2-p53 within cells forming a mass, identified expression aspect of each protein by a Western blotting after, under the same conditions above, generating a mass on said mice, processing it with ADR, and obtaining a cell lysis solution by separating the mass from the mice after 3 days. As the result, in the presence of resistance to anti-cancer agents, Mdm2 was increased and p53 level decreased (FIG. 16G).

As described above, the present invention may be utilized for studies on a mechanism by which Enigma regulates protein levels of Mdm2 and p53 through the ubiquitin-proteasome pathway, and on a mechanism by which SRF-Enigma-Mdm2-p53 pathway is regulated in cancer cells.

Furthermore, it may be utilized for developing anti-cancer agents via expression regulation of Enigma, for developing a screening method of anti-cancer agents by using Enigma expression or Enigma-Mdm2 interaction, and for developing a method of assessing the prognosis of treatment with anti-cancer agents by using Enigma expression.

As aforementioned, the Enigma overexpression causes Mdm2 stabilization and a decrease in p53, which was clearly caused by inhibition of self-ubiquitination of Mdm2 and an increase in p53 ubiquitination. Thus, it can be known that cancer cells are effectively apoptosized by inhibiting Enigma expression, that the prognosis of anti-cancer therapy may be assessed by measuring Enigma expression from cancer patients, and that substances showing anti-cancer activity may be screened by identifying a specific interaction between Enigma and Mdm2, thereby selecting substances inhibiting the interaction, thereby weakening Mdm2 stabilization and increasing p53 activity.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method of screening candidate substances for an anti-cancer agent, the method comprising:
   1) contacting PDZ and LIM domain 7 (PDLIM7) and Mdm2 in the presence or absence of a candidate substance, wherein the candidate substance is a peptide, a protein, an antibody, a small molecule, or a natural substance;
   2) measuring a binding level for PDLIM7 and Mdm2; and
   3) selecting a candidate substance that decreases the binding level for PDLIM7 and Mdm2, compared to in the absence of the candidate substance, thereby identifying an anti-cancer agent, wherein the cancer is liver cancer, stomach cancer, or colorectal cancer.

2. A method of screening candidate substances for an anti-cancer agent, the method comprising:
   1) bringing cells expressing PDZ and LIM domain 7 (PDLIM7) and Mdm2 into contact with a candidate substance;
   2) measuring a binding level for PDLIM7 and Mdm2; and
   3) selecting a candidate substance that decreases the binding level for PDLIM7 and Mdm2, compared to a control group untreated with the candidate substance, thereby identifying an anti-cancer agent, wherein the cancer is liver cancer, stomach cancer, or colon cancer.

3. A method of screening candidate substances for an anti-cancer agent, the method comprising:
   1) treating cells expressing PDZ and LIM domain 7 (PDLIM7) and Mdm2 with a candidate substance, wherein the candidate substance is a peptide, a protein, or an antibody;
   2) measuring a level of PDLIM7 or Mdm2 protein; and
   3) selecting a candidate substance that decreases stability of PDLIM7 or Mdm2 protein, compared to a control group untreated with the candidate substance, thereby identifying an anti-cancer agent, wherein the cancer is liver cancer, stomach cancer, or colon cancer.

4. The method of claim 3, wherein:
   the cells expressing PDLIM7 and Mdm2 also express Serum Response Factor (SRF) and
   wherein the candidate substance further decreases stability of SRF, compared to a control group untreated with the candidate substance.

* * * * *